US012778778B2

(12) United States Patent
Fischell

(10) Patent No.: US 12,778,778 B2
(45) **Date of Patent: *Nov. 3, 2026**

(54) SYSTEM AND APPARATUS TO ASSIST IN PRECISE STENT POSITIONING AT THE OSTIUM OF A BLOOD VESSEL

(71) Applicant: Balosmark, Inc., Kalamazoo, MI (US)

(72) Inventor: Tim Fischell, Kalamazoo, MI (US)

(73) Assignee: Balosmark, Inc., Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/409,647

(22) Filed: Dec. 4, 2025

(65) Prior Publication Data

US 2026/0083580 A1 Mar. 26, 2026

Related U.S. Application Data

(63) Continuation of application No. 19/179,942, filed on Apr. 15, 2025, now Pat. No. 12,502,295.

(60) Provisional application No. 63/634,457, filed on Apr. 15, 2024.

(51) Int. Cl.

| | |
|---|---|
| ***A61F 2/954*** | (2013.01) |
| ***A61F 2/958*** | (2013.01) |
| ***A61M 25/10*** | (2013.01) |
| *A61F 2/82* | (2013.01) |
| *A61M 25/00* | (2006.01) |

(52) U.S. Cl.

CPC .............. *A61F 2/954* (2013.01); *A61F 2/958* (2013.01); *A61M 25/1002* (2013.01); *A61F 2002/821* (2013.01); *A61M 25/005* (2013.01)

(58) Field of Classification Search

CPC .......... A61F 2/954; A61F 2/958; A61F 2/966; A61M 25/1002; A61M 25/0045; A61M 25/005; A61M 25/0023; A61M 2025/1047; A61M 2025/1045; A61M 2025/1052

See application file for complete search history.

(56) References Cited

U.S. PATENT DOCUMENTS

| | | | | |
|---|---|---|---|---|
| 5,749,890 | A * | 5/1998 | Shaknovich | A61F 2/958 606/198 |
| 5,984,946 | A * | 11/1999 | Gupta | A61M 25/10 606/194 |
| 6,458,151 | B1 | 10/2002 | Saltiel | |
| 7,651,520 | B2 * | 1/2010 | Fischell | A61F 2/95 606/108 |
| 10,258,489 | B2 | 4/2019 | Dakak | |
| 10,278,849 | B2 * | 5/2019 | Miller | A61B 34/20 |
| 10,625,059 | B2 | 4/2020 | Dakak | |
| 12,502,295 | B2 | 12/2025 | Fischell | |

(Continued)

FOREIGN PATENT DOCUMENTS

WO WO2025/221810 A1 10/2025

*Primary Examiner* — Sarah W Aleman

(74) *Attorney, Agent, or Firm* — Shay Glenn LLP

(57) ABSTRACT

Apparatuses and methods for quickly and accurately positioning a stent within the ostium of a blood vessel so that the entire circumference of the proximal stent edge is within the aorto-ostial landing zone (AOLZ). Any of these methods and apparatuses may include an ostial positioning catheter including an annular sealing balloon, a distal reinforced shaft, and a hypotube extending proximally from a longitudinal side of the distal reinforced shaft. These ostial positioning catheters may be independently operated with a guide catheter and a stent deployment catheter.

20 Claims, 17 Drawing Sheets

(56) References Cited

U.S. PATENT DOCUMENTS

2002/0133217 A1* 9/2002 Sirhan ................. A61M 25/104 623/1.11
2006/0206189 A1* 9/2006 Furst ........................ A61F 2/958 623/1.11
2006/0265041 A1* 11/2006 Sanati ........................ A61F 2/90 623/1.11
2008/0243233 A1* 10/2008 Ben-Muvhar ........... A61F 2/958 623/1.35
2009/0203962 A1* 8/2009 Miller .................... A61B 1/044 600/109
2012/0253382 A1 10/2012 Wahr et al.
2014/0277353 A1* 9/2014 Hartley ................... A61F 2/852 623/1.11
2017/0319365 A1* 11/2017 Dakak ............. A61M 25/10182
2020/0179661 A1 6/2020 Fischell et al.
2020/0289136 A1* 9/2020 Chou ..................... A61B 17/22
2023/0043660 A1* 2/2023 Palomar-Moreno .... A61F 2/958
2023/0211122 A1* 7/2023 Luna ................. A61M 25/0662 604/523
2023/0390551 A1 12/2023 Waldhauser et al.
2024/0215946 A1 7/2024 Kahlon et al.

* cited by examiner (Not to scale)

SYSTEM AND APPARATUS TO ASSIST IN PRECISE STENT POSITIONING AT THE OSTIUM OF A BLOOD VESSEL

CLAIM OF PRIORITY

This patent application is a continuation of U.S. patent application Ser. No. 19/179,942, titled "SYSTEM AND APPARATUS TO ASSIST IN PRECISE STENT POSITIONING AT THE OSTIUM OF A BLOOD VESSEL," filed on Apr. 15, 2025, now U.S. Pat. No. 12,502,295, which claims priority to U.S. Provisional Patent Application No. 63/634,457, titled "SYSTEM AND APPARATUS TO ASSIST IN PRECISE STENT POSITIONING AT THE OSTIUM OF A BLOOD VESSEL," filed on Apr. 15, 2024, each of which are herein incorporated by reference in its entirety.

BACKGROUND

Stenoses may occur at the mouth of an artery (the ostium), in which the region is substantially obstructed at its aortic take-off; this is called an aorto-ostial lesion. In such cases, the interventional cardiologist or radiologist is frequently unable to place the stent's proximal end within ±2 mm of the ostial plane. This may lead to incorrect stent positions. As a result, devices and techniques have been developed to assist in positioning the stent near the ostium. However, such devices and systems have proven difficult to use and may require size-specific considerations that make their use very difficult and inconvenient.

Accurate stent placement and balloon deployment at a stenotic site within a patient's vascular system is critical, particularly at a bifurcation site. Previously, it was believed that it was critical to maintain lumen access for insertion of marker fluid and blood flow during an angioplasty stenting procedure. See, e.g., U.S. Pat. No. 7,651,520 to Fischell et al., U.S. Pat. No. 10,258,489 to Dakak; U.S. Pat. No. 10,646,364 to Dakak, and U.S. Pat. No. 10,625,059 to Dakak. This is because is it widely believed that the complexity of accurately positioning a stent at a vessel bifurcation opening, in a pulsating circulatory system, and stenting a stenosis at a bifurcation requires a long operative time, exposing a patient and staff to extra radiation during the angiography, and injecting larger amounts of radiopaque contrast media which may compromise the patient's hemodynamic status and kidney functions, as well as allowing blood flow through or past the devices during the procedure. As a result, existing solutions have required techniques and apparatuses that leave passage for blood flow and/or require multiple spacing/inflation elements (e.g., balloons). Described herein are methods and apparatuses that may address these needs while providing a simple and elegant solution to improve stent positioning relative to an ostium.

SUMMARY OF THE DISCLOSURE

Described herein are methods and apparatuses, including systems and devices, for the treatment of disorders, including the treatment of ostial lesions. In particular, described herein are apparatuses and methods to enhance the treatment of ostial lesions via the use of a catheter with precise stent positioning. Further described herein are methods and apparatuses to assist in the precise and accurate stent positioning at the ostium of a blood vessel, thereby allowing for the enhanced treatment of ostial lesions. Still further described herein are methods and apparatuses to assist catheters (or including catheters) in the precise and accurate stent positioning at the ostium of an artery, thereby allowing for the enhanced treatment of ostial lesions. In particular, described herein are apparatuses and methods for placing stents within a stenosis that extends to or near the ostium of an artery.

Even as percutaneous coronary interventional techniques have evolved, there remains an unmet need for tools to assist in the precise placement of the proximal edge of a stent in the plane of an obstructive lesion, at the ostium of a blood vessel. This has been a particular challenge for coronary aorto-ostial lesions, such as those lesions found at the ostium of the right and left main coronary arteries.

One of the earliest patents to Saltiel (U.S. Pat. No. 6,458,151) describes a catheter with a flared distal end to try to prevent the guiding catheter from entering the target lesion or vessel. In a prior invention to Fischell et al. (U.S. Pat. No. 7,651,520), Fischell describes a nitinol device (commercially marketed as the "Ostial Pro"), with legs that could be protruded out the end of the guiding catheter to prevent the guiding catheter from entering the target vessel, to assist in precise ostial stent placement. Although this device was successful in enabling proper stent placement, there are technical challenges associated with its use that limit the adoption of the technology.

Several patents to Dakak (U.S. Pat. Nos. 10,258,489; 10,625,059; and 10,646,364) describe a variety of techniques to assist in ostial stent placement. These techniques require that there be a positioning balloon on a stent deployment catheter. This could either be for a balloon expandable or self-expanding stent. However, the placement of the positioning balloon on the stent deployment catheter is impractical, as it will require dozens of skews for different stent sizes and lengths. In another embodiment, Dakak describes placing the positioning balloon on the end of a guiding catheter. This, again, is somewhat impractical as it will require specific sizing (e.g., dozens of separate devices) for different guiding catheter shapes, as well as sizes. Moreover, the inflation lumen for the guiding catheter balloon could also compromise the inner dimension of the guiding catheter, which could limit device entry. Dakak also teaches that it is important that the ballon have an arc of less than or equal to 3400 in order to allow blood to continue to flow past the balloon. However, the methods and apparatuses described herein have surprisingly found that this limitation is unnecessary, and it may, in fact, be more beneficial to limit or restrict blood flow using an annual balloon.

Shaknovich (U.S. Pat. No. 5,749,890) describes a method and system for stent placement in ostial lesions. Shaknovich utilizes an inflatable section that touches the wall of the aorta in the vicinity of the ostium of the artery that is to be stented. As in Dakak, Shaknovich's static placement of a positioning balloon on the stent is impractical, as it requires dozens of different sizes in order to work with different stent sizes and lengths and the position of the balloon on the stent does not allow for ease of use, manipulation, and appropriate movement of the stent and the positioning balloon relative to one another and relative to the guiding catheter. Moreover, Shaknovich's positioning ballon does not integrate with the extension tube's inflation lumen or hypotube to allow for such movement and for an improved cross-section when inserting the catheter and stent.

The apparatuses (e.g., systems and devices) described herein may fully address these unmet needs and provide tools that may precisely position the proximal edge of a stent in the plane of an obstructive lesion, e.g., at the ostium of a blood vessel, while allowing for appropriate movement of the positioning balloon, guiding catheter, and stent. These apparatuses may be readily manufactured and are intuitive and easy to use and deploy.

The apparatuses and methods described herein may provide a 360-degree compliant or positioning balloon at the tip. In addition, the current invention envisions the compliant or positioning balloon extending beyond the tip of the guide extension tube such that the stent and balloon can be deployed properly, without the risk of implanting part of the stent into the guide extension tube itself. Moreover, the present invention improves upon the structural and functional connections between the compliant or positioning balloon and the extension tube's inflation lumen or hypotube to allow for appropriate movement between the two elements, ease of use, and flexible and effective deployment. Also, the methods and apparatuses described herein improve upon the overall concept with novel features such as a flattened hypotube that may significantly improve the cross-sectional area when inserted within a guiding catheter (allowing use with smaller-diameter catheters), as well as a fully functional built-in three-way stopcock integrated within the proximal end of the catheter. These and other significant advantages over the prior art will become readily apparent to one of ordinary skill that is trained in the field.

For example, described herein are apparatuses (e.g., systems) to assist in stent positioning at the ostium of a blood vessel. These apparatuses may include an ostial positioning catheter, a stent deployment catheter, a guide catheter, and may also include (or may be configured for use with) a guidewire and/or an expansion balloon catheter. In some cases, the same ostial positioning catheter may be used with multiple different stent deployment catheters and/or expansion balloon catheters. In some cases, the ostial positioning catheter may be preloaded into the guide catheter, and/or may be inserted and slid distally into position once the guide catheter is in position (with or without the use of one or more guidewires.

The ostial positioning catheter may include a distal reinforced shaft comprising a lumen extending from a distal end region to a more proximal end region. In some examples the distal reinforced shaft has a length that is less than about 20 cm (e.g., about 19 cm or less, about 18 cm or less, about 17 cm or less, about 16 cm or less, about 15 cm or less, about 14 cm or less, about 13 cm or less, about 12 cm or less, about 11 cm or less, about 10 cm or less, about 9 cm or less, about 8 cm or less, about 7 cm or less, about 6 cm or less, about 5 cm or less, about 4 cm or less, about 3 cm or less, about 2 cm or less, etc.). The ostial positioning catheter may also include an annular sealing balloon at the distal end region of the distal reinforced shaft; the annular sealing balloon may extend completely around the annuls (e.g., 360 degrees around the distal end) of the distal reinforced shaft and may be configured to extend greater than 0.1 mm (e.g., 0.1 mm or greater, 0.2 mm or greater, 0.3 mm or greater, 0.4 mm or greater, 0.5 mm or greater, 0.6 mm or greater, 0.7 mm or greater, 0.8 mm or greater, 0.9 mm or greater, 1.0 mm or greater, etc.) distal of the distal end of the distal reinforced shaft. The ostial positioning catheter may include a hypotube extending proximally from the distal reinforced shaft, wherein an inner lumen of the hypotube is fluidically coupled to the annular sealing balloon; and a proximal connector comprising an inflation hub coupled to the proximal end of the hypotube. The hypotube may couple to the ostial positioning catheter via a slit, e.g., in an outer surface of the catheter to which a flattened distal end region of the hypotube is bonded to couple to the annular inflation lumen of the distal balloon, to allow inflation of the distal ballon.

Thus, any of the ostial positioning catheters described herein may include a flattened hypotube along at least part of the length of the ostial positioning catheter. The flattened hypotube may have a rectangular or approximately rectangular (e.g., oval, elliptical, etc.) transverse cross-section. In some examples the distal reinforced shaft has a length of 2 cm or less. The proximal end of the distal reinforce shaft may be tapered. The hypotube may extend proximally from the tapered tip of the proximal end of the distal reinforced shaft. The inflation hub may be integrally coupled with the stopcock. The proximal hypotube may extend greater than about 5 cm (e.g., 8 cm or greater, 10 cm or greater, 15 cm or greater, 20 cm or greater, 25 cm or greater, etc.). The proximal connector at a distal end region of the ostial positioning catheter may comprise a stopcock configured to control flow into/out of the inner lumen of the flattened hypotube.

The ostial positioning catheter may be configured to have a very small outer diameter along its full length, including the distal ballon (e.g., in the collapsed/uninflated configuration), while having substantial column strength, e.g., able to withstand pushing against the tissue without collapse. The ostial positioning catheter may therefore be configured to be separately and independently longitudinally positionable within even a relatively small inner diameter catheter (e.g., a 6 French, 6 F, catheter or smaller).

The toroidal balloon at the distal end region of the ostial positioning catheter may be formed of a highly compliant, thin yet durable biocompatible material. The ballon may be formed of a material having a durometer of between about 5 ShoreA and about 75 ShoreA (e.g., between about 5 ShoreA and about 60 ShoreA, etc.). Examples of such materials may include, but are not limited to: medical-grade Styrene Ethylene Butylene Styrene (SEBS) thermoplastic elastomers (TPEs) such as SEBS Proflex™, medical-grade thermoplastic polyurethanes (TPUs) such as Chronoprene® and/or Rezalloy™ and/or Pellethane™, medical-grade thermoplastic polyesters such as Neusoft™, a thermoplastic vulcanizate (TPV) such as Santoprene™ or other polypropylene (PP) thermoplastic matrix materials that include dynamically vulcanized EPDM rubber and or a blend including one or more of these such as PolyBlend™.

Further, the ostial positioning catheter may be configured to work with a variety of sizes (diameters and/or lengths) of stent deployment catheters, at least in part due to the outer diameter of the lumen of the distal reinforced shaft of the ostial positioning catheter. The lumen of the ostial positioning catheter may be any appropriate diameter (e.g., between about 0.1 mm to 1 cm, e.g., between 0.1 mm to 5 mm, etc.). The ostial positioning catheter may remain highly steerable and flexible, even within the tortious anatomy of the vasculature, because the distal reinforced shaft of the ostial positioning catheter may be a relatively short length (e.g., about 19 cm or less, about 18 cm or less, about 17 cm or less, about 16 cm or less, about 15 cm or less, about 14 cm or less, about 13 cm or less, about 12 cm or less, about 11 cm or less, about 10 cm or less, about 9 cm or less, about 8 cm or less, about 7 cm or less, about 6 cm or less, about 5 cm or less, about 4 cm or less, about 3 cm or less, about 2 cm or less, etc.) relative to the overall length. The proximal hypotube may be flexible yet may provide sufficient column strength to allow pushing/pulling, including driving the inflated annular balloon against/around the ostium to seal the ostium. Sealing around an ostium may counterintuitively improve the procedure, maintaining sufficient space for deployment of the stent (without interference) while stabilizing the stent deployment.

For example an apparatus (e.g., device, system, etc.) may be configured as an apparatus for applying a stent to an ostium of a blood vessel, and may include: a distal reinforced shaft having a length that is 10 cm or less, the distal reinforce shaft comprising a lumen configured to slidingly receive a stent deployment catheter therein, the lumen extending from an open distal end to an open proximal region of the distal reinforced shaft; an annular sealing balloon at a distal end region of the distal reinforced shaft, the annular sealing balloon extending 360 degrees around the distal end of the distal reinforced shaft and configured to extend distal of the distal end of the distal reinforced shaft when the annular sealing balloon is inflated; a hypotube extending proximally from the distal reinforced shaft, the hypotube comprising a hypotube lumen of that is fluidically coupled to the annular sealing balloon, wherein the hypotube has a length that is greater than the length of the distal reinforced shaft; and a proximal connector comprising an inflation hub coupled to the proximal end of the hypotube.

The distal region of the hypotube may be flattened. For example, the flattened distal region of the hypotube may engage with a longitudinal slot through a wall of the reinforced shaft so that the hypotube lumen is in fluid communication with an inflation path through a wall of the distal reinforced shaft that is in fluid communication with the annular sealing balloon. In some cases, the flattened hypotube has a rectangular or elliptical transverse cross-section.

In general, the hypotube may be longer than the distal reinforced shaft. For example, the hypotube length may be 1.5 times, 2 times, 2.5 times, 3 times, 3.5 times, 4 times, 5 times, 6 times, 7 times, 8 times, 9 times, 10 times, or more the length of the distal reinforced shaft. In some cases, the distal reinforced shaft may be 5 cm or less (e.g., 4 cm or less, 3 cm or less, 2 cm or less, etc.). For example, the proximal hypotube may extend greater than 10 cm (12 cm or greater, 15 cm or greater, 20 cm or greater, 25 cm or greater, 30 cm or greater, 35 cm or greater, 40 cm or greater, 50 cm or greater, 75 cm or greater, 80 cm or greater, 90 cm or greater, 1 m or greater, etc.).

In any of these examples the distal reinforced shaft may be more flexible than the hypotube. In some cases, the hypotube may be laser cut (and sealed, e.g., by a polymeric material) to enhance flexibility without significantly decreasing pushability (e.g., column strength).

The open proximal region of the distal reinforce shaft may be tapered, as described herein. The taper may be linear or curing. The taper may be formed of an interface region (e.g., polymeric interface region) and may be configured to couple to the hypotube (e.g., the flattened hypotube). The hypotube may extend proximally from a tapered tip of the proximal region of the distal reinforced shaft (in some cases the proximal region of the distal reinforced shaft may be formed by the interface region).

The distal reinforced shaft may be reinforced in any appropriate manner, including having one or more helically-wound (e.g., metal, polymeric) reinforcements, rings, braids, etc. For example, the distal reinforced shaft may comprise a reinforcing braid (over which a polymeric material may be reflowed).

In general, the annular sealing balloon may be configured to seal around an annulus when inflated. The annular sealing balloon may have a distal-facing surface (annular distal-facing surface) and a proximal-facing surface (annular proximal-facing surface). The distal-facing surface may be configured to seal around an ostia when in use.

In any of these examples, the lumen of the distal reinforced shaft may comprise a lubricious (e.g., hydrophilic) outer surface, such as a lubricious coating or material (sleeve, etc.). In some cases, the distal reinforced shaft may be formed of a lubricous material or embedded with a lubricous additive.

The inflation hub may be integrally coupled with one or more valves (e.g., a stopcock). Thus, the proximal connector may comprise a stopcock configured to control flow into/out of the inner lumen of the flattened hypotube.

In general, the ostial positioning catheter may be configured to have a relatively small outer diameter (with the balloon deflated) so that they can be inserted through a narrow guide catheter. This is possible because of the construction of the distal reinforced shaft and the off-axis hypotube. For example, in some cases the maximum outer diameter of the apparatus (with the annular sealing balloon un-inflated) is about 8 F or smaller (about 7 F or smaller, about 6 F or smaller, etc.). As mentioned, the hypotube may be mounted off-axis with the distal reinforced shaft, so that the hypotube extends in-line with one side of the distal reinforced shaft.

In any of these apparatuses the hypotube may have an outer diameter than is less than half of the outer diameter of the distal reinforced shaft (e.g., less than 45% of the outer diameter, less than 40% of the outer diameter, less than 35% of the outer diameter, less than 30% of the outer diameter, less than 25% of the outer diameter, less than 20% of the outer diameter, less than 15% of the outer diameter, less than 10% of the outer diameter, etc.).

As mentioned, any of these hypotube portions of the ostial positioning catheter may have a flattened region (for interfacing with the distal reinforced shaft, e.g., in a slot/slide of the reinforced shaft) and a non-flattened region. The non-flattened hypotube region may have a generally circular cross-section while the flattened hypotube has a generally elliptical and/or rectangular shape. In both flattened and un-flattened regions of the hypotube, the lumen (inflation lumen for the annular balloon) may remain open to allow fluid to inflate/deflate the annular balloon. The hypotube may be generally un-flattened along the majority of its length; e.g., just the distal 40%, 30%, 20% 10%, 9%, 8%, 7%, 6%, 5%, 4%, 3%, 2% or less may be flattened.

For example, an apparatus for applying a stent to an ostium of a blood vessel may include: a distal reinforced shaft having a length, the distal reinforce shaft comprising a lumen configured to slidingly receive a stent deployment catheter therein, the lumen extending from an open distal end to an open proximal region of the distal reinforced shaft; an annular sealing balloon at a distal end region of the distal reinforced shaft, the annular sealing balloon extending 360 degrees around the distal end of the distal reinforced shaft and configured to extend distal of the distal end of the distal reinforced shaft when the annular sealing balloon is inflated; a hypotube extending proximally from the distal reinforced shaft, the hypotube comprising distal flattened region engaged within a longitudinal slot within a wall of the distal reinforced shaft so that a lumen extending through the hypotube is fluidically coupled to the annular sealing balloon through the wall, wherein the hypotube has a length that is at least twice a length of the distal reinforced shaft; and a proximal connector comprising an inflation hub coupled to the proximal end of the hypotube.

An apparatus for applying a stent to an ostium of a blood vessel may include: a distal reinforced shaft having a length that is 10 cm or less, the distal reinforce shaft comprising a lumen configured to slidingly receive a stent deployment catheter therein, the lumen extending from an open distal end to an open proximal region of the distal reinforced shaft; an annular sealing balloon at a distal end region of the distal reinforced shaft, the annular sealing balloon extending completely around the distal end of the distal reinforced shaft and configured to extend distal of the distal end of the distal reinforced shaft to seal over an ostium when the annular sealing balloon is inflated; a hypotube extending proximally and off-axis from an open proximal region of the distal reinforced shaft, the hypotube comprising a hypotube lumen of that is fluidically coupled to the annular sealing balloon, wherein the hypotube has a length that is greater than the length of the distal reinforced shaft; and a proximal connector comprising an inflation hub coupled to the proximal end of the hypotube; wherein the outer diameter of the apparatus is less than 8 French when the annular sealing balloon is uninflated.

Also described herein are systems including any of these ostial position catheters. For example, a system for applying a stent to an ostium of a blood vessel may include: a guide catheter having a guide catheter lumen; an ostial positioning catheter configured to slideably fit within the guide catheter lumen, the ostial positioning catheter comprising a distal reinforced shaft having a length of less than 10 cm and a lumen extending therethrough, an annular sealing balloon at a distal end region of the distal reinforced shaft, and a hypotube extending proximally from a longitudinal side of the distal reinforced shaft, wherein the hypotube comprises an inflation lumen in fluid communication with the annular balloon through the distal reinforced shaft; and a stent deployment catheter configured to slideably fit within the ostial positioning catheter, the stent deployment catheter comprising a stent over a deployment balloon.

The system may include one or more guidewires configured to fit through a lumen of the stent deployment catheter.

The stent deployment catheter may be preloaded with the ostial positioning catheter and/or the guide catheter, and/or the guide catheter may be preloaded with the ostial positioning catheter. For example, the stent deployment catheter may extend through the lumen of the ostial positioning catheter and further wherein the ostial positioning catheter extends through the guide catheter lumen.

Also described herein are methods of positioning a stent (using any of these apparatuses). For example, a method of positioning stent may include: positioning a guide catheter at an ostia of a blood vessel; advancing a stent delivery catheter through the guide catheter and into the ostia; advancing an ostial positioning catheter through the guide catheter and over the stent delivery catheter so that a distal end of the ostial positioning catheter is proximal to the ostia and outside of the guide catheter; inflating an annular, toroidal balloon of the ostial positioning catheter; holding the distal side of the annular, toroidal balloon against a tissue around the ostia; moving the stent deployment catheter through the ostial positioning catheter to align a proximal end of a stent on the stent deployment catheter with the annular, toroidal balloon; deploying the stent from the stent delivery catheter to expand the coronary artery; and deflating the annular, toroidal balloon and withdrawing the ostial positioning catheter through the guide catheter.

Positioning the guide catheter at the ostia of the blood vessel may comprise positioning the guide catheter at the ostia of a coronary artery. For example, positioning the guide catheter may comprise using a guidewire to position the guide catheter at the ostia of the blood vessel.

In any of these methods holding the distal side of the annular, toroidal balloon against the tissue around the ostia may comprise pushing the guide catheter distally against a proximal face of the annular, toroidal balloon. Alternatively or additionally, holding the distal side of the annular, toroidal balloon against the tissue around the ostia may comprise driving the ostial positioning catheter distally.

Any of these methods may include inserting the stent delivery catheter through the ostial positioning catheter within the lumen of the guide catheter. For example, inserting may comprise inserting through a distal reinforced shaft of the ostial positioning catheter that extends 10 cm of less.

Any of these methods may include flaring the proximal end of the stent, e.g., by withdrawing the stent delivery catheter proximally and expanding the stent delivery catheter to further expand the proximal end of the stent. The method may also include withdrawing the stent delivery catheter proximally through the guide catheter.

In any of these methods, aligning the proximal end of the stent on the stent deployment catheter with the annular, toroidal balloon may comprise aligning the proximal marker of the stent delivery system with a radio-opaque tip marker of the ostial positioning catheter.

Any of these methods may include pre-treating the stenotic region of the ostia to crack or weaking the stenosis, e.g., by inserting an expansion ballon catheter from the guide catheter into the ostia before advancing the stent delivery catheter into the ostia, then expanding the expansion ballon catheter to break a stenosis within the ostia and then withdrawing the expansion ballon catheter out of the guide catheter.

In some examples a method may include: positioning a distal end of a guide catheter (optionally using a guidewire) at an ostia of a coronary artery; advancing a stent delivery catheter through the guide catheter and into the coronary artery; advancing an ostial positioning catheter through the guide catheter so that a distal end of the ostial positioning catheter is positioned just proximal to the ostia of the coronary artery and outside of the guide catheter; inflating an annular, toroidal balloon of the ostial positioning catheter; sealing the distal side of the annular, toroidal balloon completely around the ostia; optionally holding a distal end of the guide catheter against a proximal side of the annular, toroidal balloon; aligning the proximal end of the stent with an edge of the annular, toroidal balloon (e.g., by pulling the stent deployment catheter proximally until stopped against the toroidal balloon of the ostial positioning catheter); deploying the stent using the stent deployment catheter so that it expands (e.g., by expanding a deployment balloon of the stent delivery deployment catheter) within the coronary artery, optionally while maintaining the longitudinal position of the stent delivery catheter (e.g., by maintaining the proximal pull on the stent delivery catheter); deflating the annular, toroidal balloon; and withdrawing the ostial positioning catheter proximally through the guide catheter. Optionally the proximal mouth of the stent may be flared slightly, e.g., by partially withdrawing the stent deployment catheter proximally, then re-expanding the deployment balloon of the stent deployment catheter. The stent deployment catheter may then be fully withdrawn, leaving the stent in position within the ostium.

Optionally, the ostium may be expanded, e.g., using an expansion balloon catheter, prior to inserting the stent deployment catheter into the ostium. Any of these methods may include extending the guide wire through the ostia into the coronary artery. For example, positioning the guide catheter may comprise using a guidewire. Any of these methods may include inserting the stent deployment catheter through the ostial positioning catheter while it is within the lumen of the guide catheter; alternatively, the stent deployment catheter may be preloaded into the ostial positioning catheter. Inserting may comprise inserting through a distal reinforced shaft extending less than 10 cm.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 2A shows a perspective view of the ostial positioning catheter with the annular balloon expanded. FIG. 2B shows an enlarged perspective view of the distal reinforced region of the ostial positioning catheter without the proximal hypotube portion attached. FIGS. 2C and 2D shows side and top views, respectively, of the proximal hypotube portion of the ostial positioning catheter. FIG. 2E shows an end view of the proximal hypotube portion shown in FIGS. 2C and 2D. FIG. 2F is a top view of a distal portion of the ostial positioning catheter of FIGS. 2A-2E. FIG. 2G is a side sectional view of the ostial positioning catheter of FIG. 2F. FIG. 2H shows an end view (from the distal end) of the ostial positioning catheter of FIGS. 2A-2G.

DETAILED DESCRIPTION

Figure 1A:
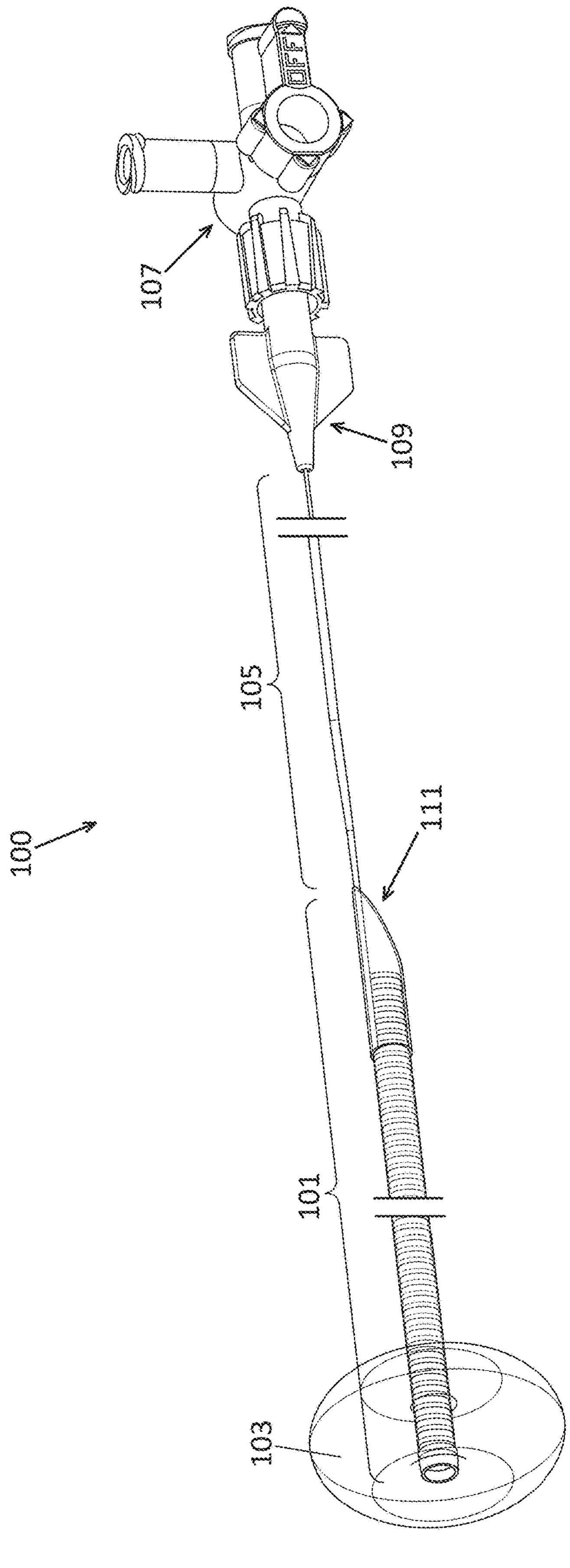
FIG. 1A shows an example of an ostial positioning apparatus (e.g., an ostial positioning catheter) that may be used to assist in stent positioning at an ostium.

In general, described herein are apparatuses and methods for positioning a stent at the ostium of a blood vessel. For example, these methods and apparatuses may quickly and accurately position a stent within the ostium so that the entire circumference of the proximal stent edge is within the aorto-ostial landing zone (AOLZ), which is the region along the coronary arteries axis that is within about one millimeter of the aorto-ostial plane. Correct positioning may increase the likelihood of restenosis and lead to further complications. The methods and apparatuses described herein may be performed over a larger variety to patient anatomies and may be performed more quickly than conventional techniques.

In general, any of these methods and apparatuses may include an ostial positioning catheter, a stent deployment catheter, a guide catheter, and may also include (or may be configured for use with) a guidewire and/or an expansion balloon catheter. Each of these components, including in particular the ostial positioning catheter, may be independently moved in the proximal-to-distal direction during operation. The ostial positioning catheters described herein may include particular features enhancing their use and operation.

For example, any of the ostial positioning catheters described herein may generally include an inflatable sealing annular balloon that may be precisely positioned at the distal end of the ostial positioning catheter. In some examples the inflatable sealing annular balloon, once inflated, projects slightly distally (e.g., about 0.5 mm, +/−0.1 mm) distal of the distal end of the ostial positioning catheter, which may allow sufficient room for the stent, without interfering with stent deployment. The inflatable sealing annulus (e.g., annular balloon, such as a toroidal balloon) may be configured to seal fully against the region around the ostium. The apparatus may include a distal reinforced shaft that is tubular, forming an inner lumen (e.g., the ostial positioning catheter lumen) that may be open at both the proximal region and at the distal end. The proximal opening may be near the distal (or an intermediate) region of the ostial positioning catheter. This distal reinforced shaft may preferably be between about 1 cm and 20 cm (e.g., 20 cm or less, 15 cm or less, 12 cm or less, 10 cm or less, 9 cm or less, 8 cm or less, 7 cm or less, 6 cm or less, 5 cm or less, 4 cm or less, 3 cm or less, 2 cm or less, 1 cm or less, 1.5 cm or less, between about 1 cm and 1.5 cm, between about 1 cm and 2 cm, etc.). The distal reinforced shaft may be coupled at its proximal end to a proximal hypotube shaft that may be mounted off-axis, allowing other devices to be easily inserted into/through the lumen of the distal reinforced shaft. The hypotube shaft may be an appropriate length (e.g., between about 2 cm and 1.5 m, between about 5 cm and 70 cm, between about 5 cm and 60 cm, between about 5 cm and 50 cm, etc.). The proximal hypotube may include an inflation lumen that is fluidly coupled with the inflatable sealing annulus (e.g., balloon) at the distal end of the apparatus. The proximal end of the proximal hypotube shaft may be coupled to an inflation hub that is coupled with a stopcock to allow the application of pressure (positive and/or negative pressure and/or exposure to atmosphere/venting) to control the inflation state of the inflatable sealing annulus.

Figure 3A:
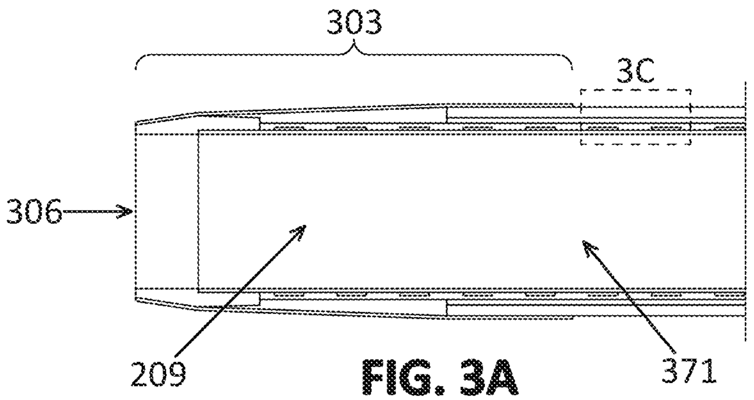
FIGS. 3A and 3B illustrate an example of a distal end region of an apparatus such as the one shown in FIG. 1, in an undeployed (FIG. 3A) and deployed (FIG. 3B) configuration. In the deployed configuration, the annular balloon is inflated, providing a complete sealing surface for positioning against the ostium and a spaced region to allow deployment of a variety of differently sized stents.
Figure 3B:
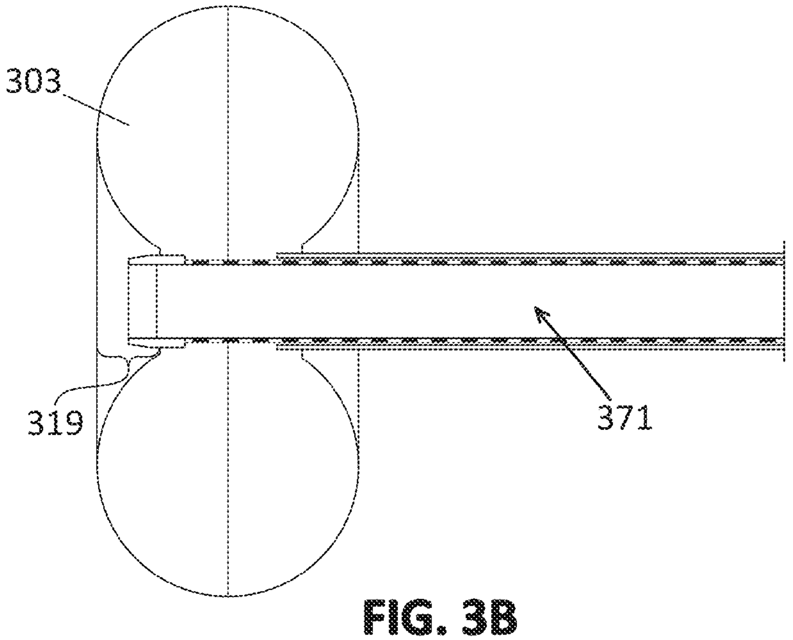
Figure 4A:
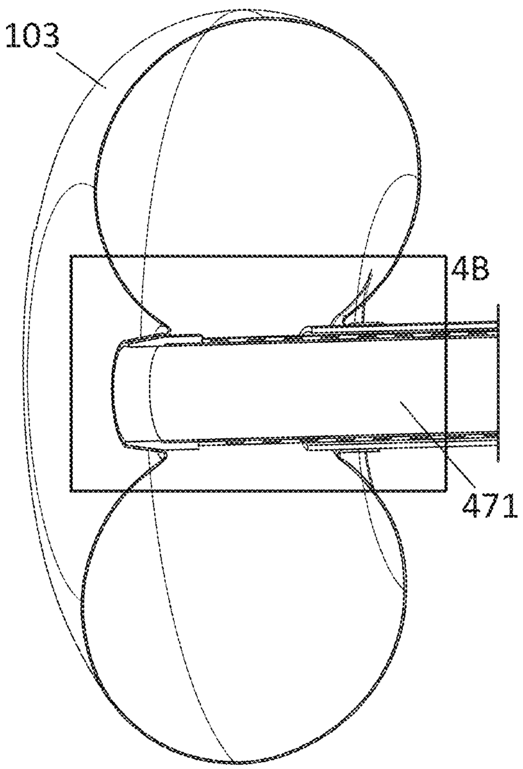
FIG. 4A is another example of the distal end region of the apparatus shown in a deployed (e.g., inflated) configuration.
Figure 4B:
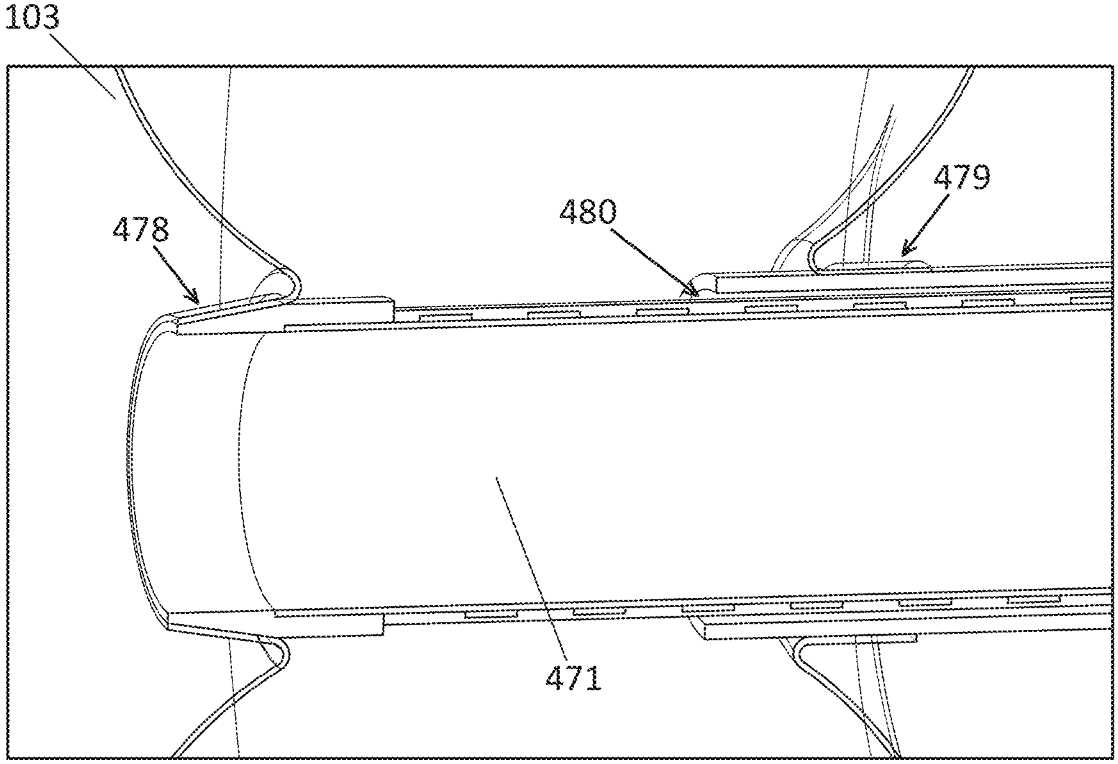
FIG. 4B shows an enlarged view of the hub region of the distal end.

FIG. 1 shows an example of an ostial positioning catheter 100 of an apparatus as described herein. In this example, the ostial positioning catheter includes a distal reinforced shaft 101 having a lumen (e.g., an ostial positioning catheter lumen) extending from a distal end to a proximal end of the reinforced shaft. The ostial positioning catheter also includes an annular balloon 103 at the distal end region of the distal reinforced shaft. The annular balloon may be an annular sealing balloon, e.g., configured to seal around an ostium, extending completely around (e.g., 360 degrees around) the distal end of the distal reinforced shaft. The balloon may be toroidal and may be configured to extend beyond the distal end of the ostial positioning catheter when the balloon is inflated. For example, the balloon may extend more than 0.5 mm distal of the distal end of the distal reinforced shaft, as shown in FIGS. 3B and 4A-4B. The ostial positioning catheter may also include a proximal hypotube region 105 extending proximally from the distal reinforced shaft (in this example, from a proximal-most end of the proximally tapered shaft 101). Thus, the elongate body of the ostial positioning catheter may be configured as a relatively small diameter hypotube, which may be flexible and may include an inner lumen (e.g., inflation lumen). The inner lumen of the hypotube may be fluidically coupled to the annular sealing balloon to inflate/deflate the balloon.

As will be described in detail below, the hypotube may include a distal flattened region that may engage with a slit or slot within the reinforced region in the wall of the outer catheter body formed by the reinforced region. This may allow inflation of the annular balloon, which may also be referred to equivalently as a distal positioning balloon. The annular balloon may be coated with and/or may integrate, a hydrophilic coating.

The ostial positioning catheter also includes a proximal handle and/or connector that may include an inflation hub 109 coupled to the proximal end of the hypotube. The connector in this example also includes a stopcock 107 to control application of fluid to inflate/deflate the balloon.

Figure 1B:
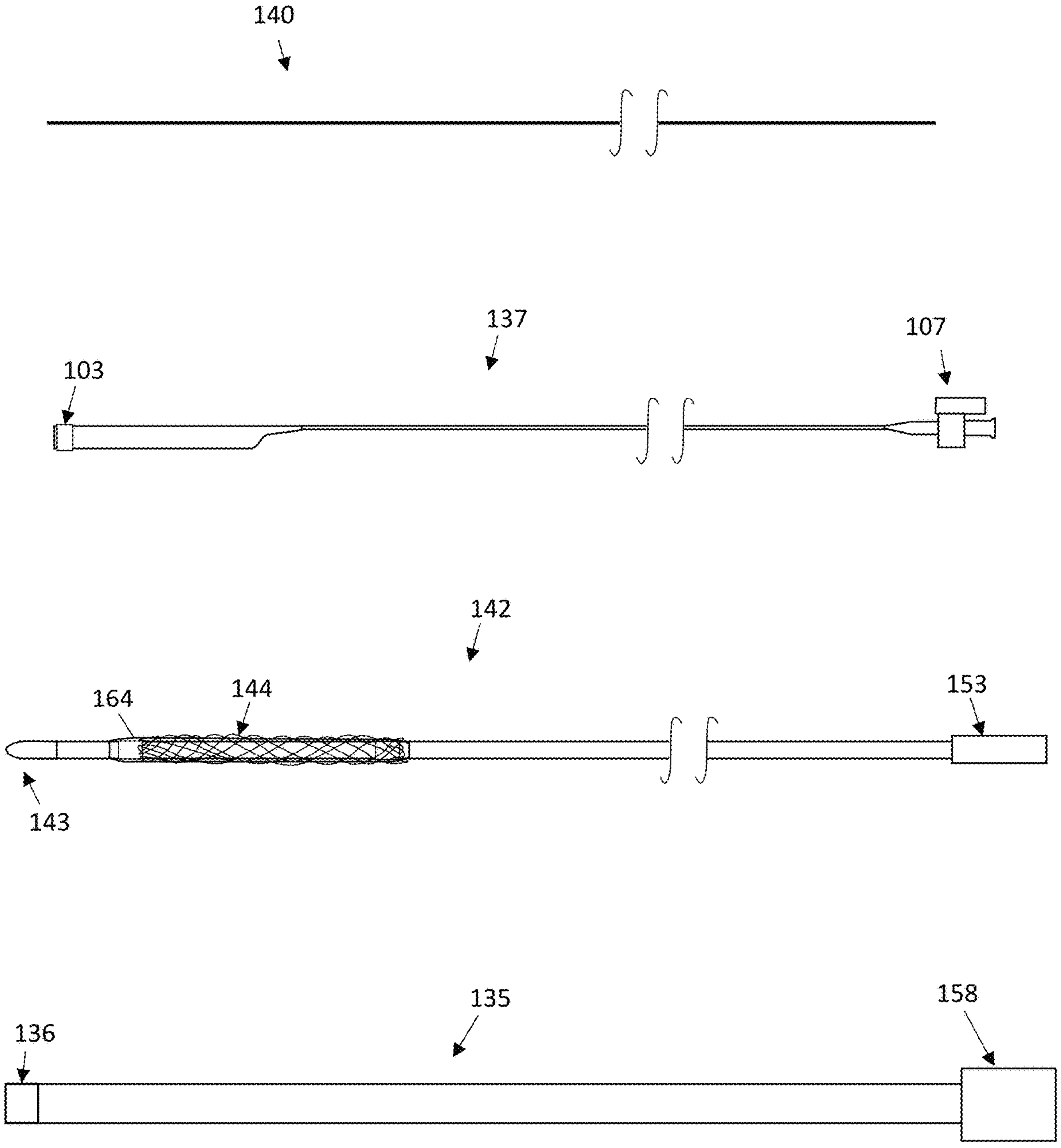
FIG. 1B shows an example of a system including an ostial positioning catheter such as the one shown in FIG. 1A.

An ostial positioning catheter such as the one shown in FIG. 1A may be part of an apparatus, e.g., a system, including a guide catheter and one or more stent deployment catheter. For example, FIG. 1B illustrates one example of a system including an ostial positioning catheter 137, similar to that shown in FIG. 1A, as well as a stent deployment catheter 142 and a guide catheter 135. The system may also optionally include one or more guidewires 140. In general, the ostial positioning catheter 137 may fit into the lumen of the guide catheter 135 (guide catheter lumen) and may be inserted from the proximal end. The stent deployment catheter 142 may fit the lumen of the ostial positioning catheter 137 (e.g., the ostial positioning catheter lumen). A guidewire may fit through the lumen of the stent deployment catheter 142, and/or the ostial positioning catheter 137, and/or the guide catheter 135. In some cases, the system may also include one or more additional members, such as (but not limited to) an expansion balloon catheter (not shown) that may be used to expand the lumen of the ostium prior to inserting the stent deployment catheter, particularly where the lesion is highly calcified.

The ostial positioning catheter 137 shown in FIG. 1B may include a reinforced distal end region as described in FIG. 1A, which may form the ostial positioning catheter lumen into which a stent deployment catheter may fit. The ostial positioning catheter lumen may extend a relatively short distance (e.g., between 5 mm and 30 cm, e.g., between 5 mm and 25 cm, between 5 mm and 20 cm, between 5 mm and 15 cm, between 5 mm and 10 cm, between 1 cm and 15 cm, between 5 cm and 12 cm, etc.). The proximal end of the reinforced region may be tapered, as shown in FIGS. 1A and 1, which may enhance engagement with the stent deployment catheter. The ostial positioning catheter 137 also include an annular balloon 103, as described above. The proximal end may include a handle and/or hub (with or without one or more valves/stopcock 107) coupled to the proximal end of the hypotube.

Any appropriate stent deployment catheter 142 may be used. For example, the stent deployment catheter may include an elongate stent body having an atraumatic (e.g., tapered) distal tip region 143. The stent deployment catheter may enclose a lumen (not shown) for passing a guidewire. The stent deployment catheter may also include a stent deployment balloon 164 and a stent 144, so that expanding the stent deployment balloon may expand and deploy the stent 144. Any appropriate stent may be used, having any appropriate length. In some cases, the stent may be nickel-titanium stent. The stent deployment catheter may also include an inflation lumen for controlling expansion of the stent deployment lumen. The proximal end of the stent deployment catheter may include one or more connections, including connection to a source of fluid to expand the balloon and/or pressure release (e.g., a hub). The proximal end may also or alternatively include a handle or grip 153 region. In general, the outer diameter of the stent deployment catheter may be configured to fit within the lumen of the ostial positioning catheter. As an example only, the inner diameter of the ostial positioning catheter may be between about 0.03" and 0.2" (e.g., between about 0.04" and 0.15", between about 0.04" and 0.08", etc.). As an example only, the outer diameter of the ostial positioning catheter may be between about 0.04" and 0.25" (e.g., between about 0.04" and 0.2", between about 0.04" and 0.15", between about 0.04" and 0.08", between 0.04 and 0.07", e.g., 8 F or smaller, 7 F or smaller, 6 F or smaller, etc.).

Any appropriate guide catheter 135 may be used. In general, the inner diameter of the guide catheter 135 may be larger than the outer diameter of the ostial positioning catheter 137 (and the stent deployment catheter). The distal end of the guide catheter may include a soft/atraumatic distal tip region 136. The guide catheter may include a handle and/or hub at the proximal end. In some cases, the guide catheter may include an integrated hemostasis valve or may be configured for use with a hemostasis valve.

In FIG. 1B the system may include one or more guidewires 140, including pre-bent or curved guidewires (e.g., J-wires, etc.). In some examples the guidewire may include a handle or grip.

Figure 2A:
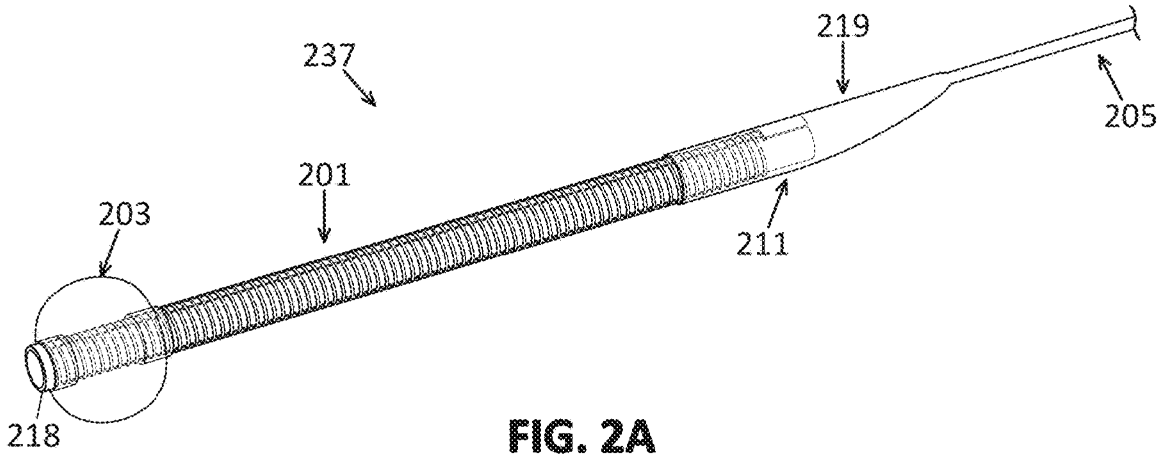
FIGS. 2A-2H illustrate another example of an ostial positioning catheter.
Figure 2B:
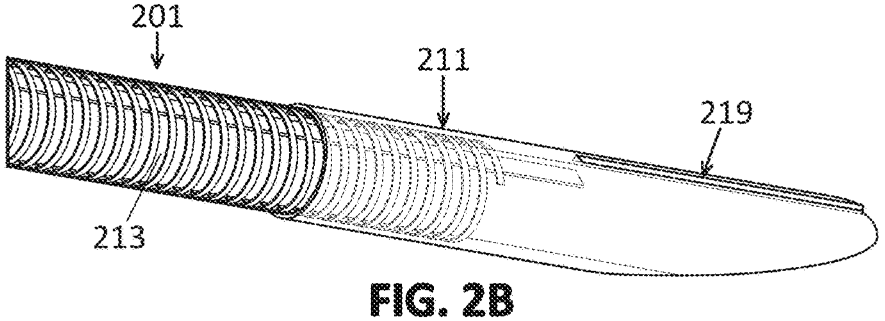

FIGS. 2A-2H illustrate another example of an ostial positioning catheter 237, similar to that shown in FIG. 1A, and which may also be used with (or as part of a system including) a guide catheter and stent deployment catheter. In FIG. 2A the ostial positioning catheter 237 includes a distal tip 218 at the distal end of a reinforced shaft 201. The reinforced shaft may be formed of a polymeric material surrounding a more rigid reinforcement, such as a coil (e.g., helical coil winding), providing both a high degree of flexibility with radial support. The ostial positioning catheter 237 also includes an annular balloon 203 at the distal end region of the ostial positioning catheter 237. The balloon in FIG. 2A is shown inflated and does not extend distally beyond the distal tip. As discussed above, in some examples the balloon may extend distally beyond the distal tip. The ostial positioning catheter 237 in FIG. 2A also includes a proximal hypotube region 205 that is coupled to the reinforced region 201 at an interface assembly 211 (shown in greater detail in FIG. 2B) that forms the tapered opening into the lumen ostial positioning catheter. The lumen of the ostial positioning catheter 237 is formed by the reinforced region. The interface assembly may be formed over, and/or bonded or otherwise secured to, the reinforced region. In any of these examples the hypotube, which includes the inflation lumen for the annular balloon 203, may be configured to engage with the reinforced distal region of the ostial positioning catheter through an inflation lumen slot or slit 209 that extends through the outer portion of the ostial positioning catheter and into the inflation lumen portion of the reinforced region, which may be, e.g., between an outer layer and an inner layer, either or both of which may be reinforced. For example, the hypotube shaft may be flattened at or near its distal end region and may fit and open into the attachment slot 219 of the interface assembly 211. This attachment slot may therefore be configured to put the lumen of the hypotube in fluid communication with the lumen portion of the inflation lumen (radially outward from the inner lumen of the ostial positioning catheter). In some examples the attachment slot lumen may have a dimension of, e.g., 0.001"×0.010" (e.g., approximately 0.00001 square inches). In some cases, the interface assembly may be formed of the same polymeric material as the reinforced shaft 201, e.g., polyimide. The inflation lumen may be formed through the reinforcement shaft and may be fluidically continuous with the attachment slot of the interface assembly. In some cases, the interface assembly is not needed, and the hypotube may be connected directly to the reinforcement shaft.

In some cases, the reinforcement shaft may be formed as a metal reinforced region (e.g., reinforcement coil 213) over which a polymeric material has been reflowed. In some cases, the reinforced region 201 may be formed of two co-axial layers (catheters) and the inflation lumen for the annular balloon may be between the co-axial layers; as mentioned, either or both layers may be reinforced. Alternatively, the inflation lumen may be formed of just a polymer region (without reinforcement).

Figure 2C:
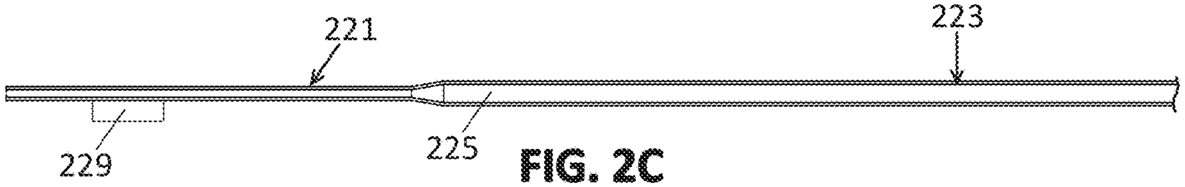
Figure 2D:
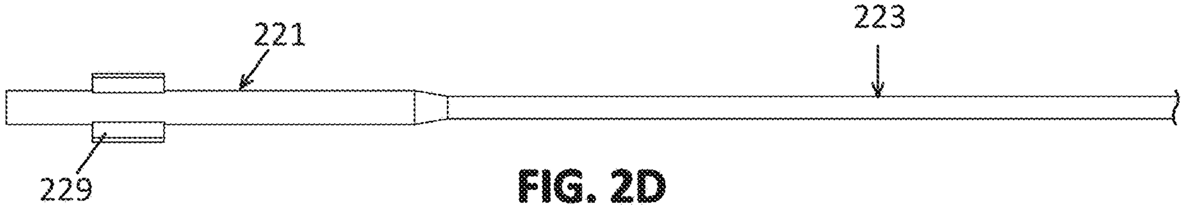

As mentioned, the proximal region may be formed of a metal hypotube, an example of which is shown in FIGS. 2C and 2D. In FIGS. 2C-2D, the inflation hypotube 223 includes an inflation lumen 255 and the distal end region is flattened to form a flattened portion of the hypotube 221 that may be crimped at its distal end and inserted within the attachment slot 219. The inflation lumen slot may be sealed to the flattened hypotube; in some cases, the polymeric material forming the reinforced shaft 201 and/or interface assembly may be reflowed around the region of the flattened hypotube in the slot to seal the inflation lumen.

They flattened distal region of the hypotube 221 includes a lumen that is continuous with the lumen of the inflation hypotube, forming the inflation lumen 225 that may be used to inflate/deflate the annular balloon 203. In any of these examples the hypotube may extend proximally for the majority of the length of the ostial positioning catheter 237. The distal end (e.g., the flattened hypotube region 221) may be coupled to the reinforced region 201 by one or more interface attachments 229, e.g., welds.

Figure 2E:
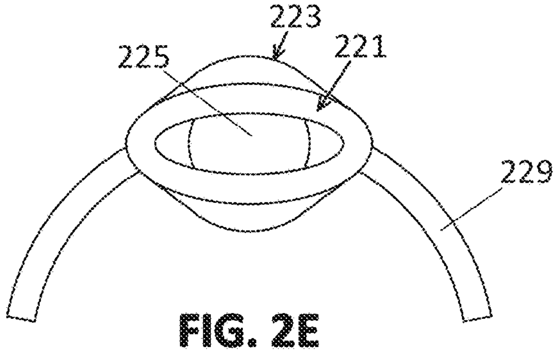

FIG. 2E shows an end view of just the hypotube, including both the flattened region 221 and the non-flattened region 223, showing the inner lumen 225 extending along the length. The flattened region may have a rectangular or rounded (e.g. oval, elliptical, etc.) cross-section. In general, the flattened hypotube may have a larger width than height (e.g., a ratio of width to height of 1.5 or greater to 1, 2 or greater to 1, 2.5 or greater to 1, 3 or greater to 1, 4 or greater to 1, etc.). The use of the hypotube and flattened distal region may preserve the column strength (e.g., pushability) of the ostial positioning catheter, without detracting from the flexibility and small size of the ostial positioning catheter.

Figure 2F:
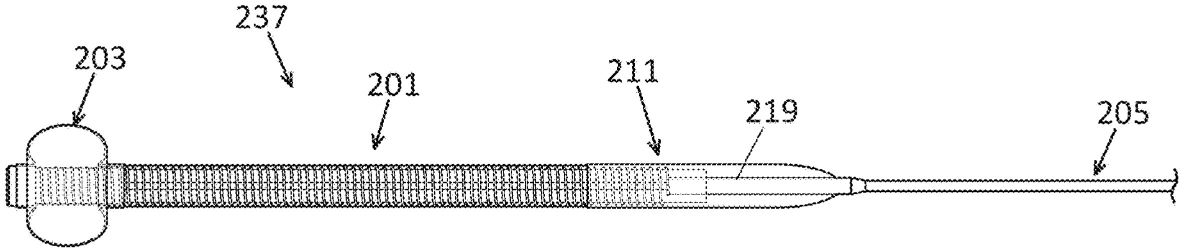
Figure 2G:
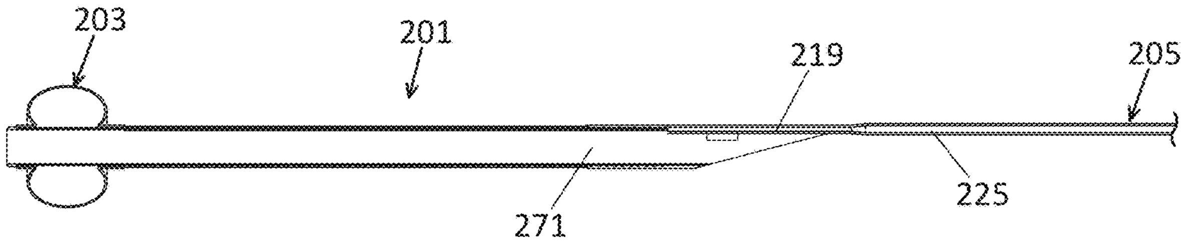

FIGS. 2F and 2G show side and side sectional views, respectively. In FIG. 2F, the ostial positioning catheter 237 includes the inflated distal balloon 203, reinforced shaft distal region 201, attachment interface region and attachment slot 219, and proximal hypotube region 205. The ostial positioning catheter lumen 271 is shown extending through the reinforced region in FIG. 2G. FIG. 2G also shows the inflation lumen 225 extending through the proximal hypotube region 205.

Figure 2H:
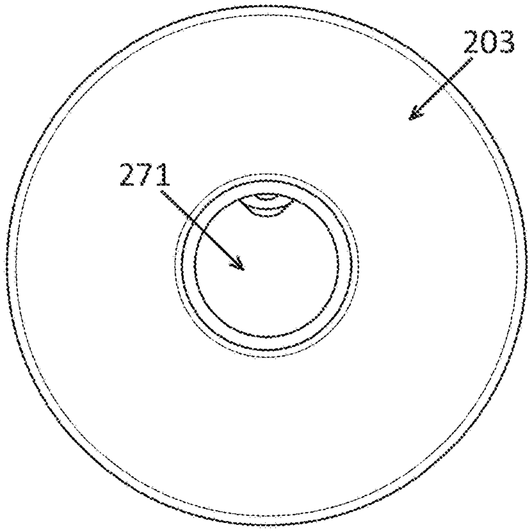

In general, the annular balloon 203 may be configured to inflate through the wall of the ostial positioning catheter, as fed by the coupling between the flattened hypotube and the reinforced region 201 at the slot/slit 219. In some cases, the balloon may extend past the tip of the catheter, only when inflated. The annular balloon 203 may be configured to engage with the wall forming the ostium. FIG. 2H shows an end view of the annular balloon 203 surrounding the opening into the lumen 271 of the ostial positioning catheter. The shape of the annular balloon 203 may be configured to engage with the ostium. For example, the shape of the annular balloon may allow it to engage with a guide catheter on the proximal side (as shown in FIGS. 12C-12D and 13H-13K, described below), and on the distal side with the stent.

In general, the annular balloon may be formed of an ultra-compliant, synthetic latex-like material which may allow it to increase in size by between 3.5 to 6 times (e.g., between about 4-5×), while also rebounding back to the original (or nearly original) outer diameter in the deflated configuration, so that it may readily fit back through the guide catheter upon withdrawal. For example, the annular balloon may be configured to inflated to an outer diameter of at least 3 mm (e.g., at least 3.5 mm, at least 4 mm, at least 4.5 mm, at least 5 mm, at least 5.5 mm, at least 6 mm, at least 6.6 mm, at least 7 mm, etc.) with less than 0.3 mL of inflation fluid (e.g., 0.5 mL or less, 0.5 mL or less, 0.6 mL or less, 0.7 mL or less, 0.8 mL or less, 0.9 mL or less, 1 mL or less, etc.).

In operation, the annular balloon may seal off the ostium, occluding and preventing blood flow during the procedure, which may also beneficially prevent contract from leaving. The annular configuration may also enhance stability with the ostium, preventing variations due to movement (including heart motions) during use, particularly when holding the annular balloon against the ostium (by applying force from the guide catheter) which is not possible with conventional techniques. This may allow the use of contrast to create a static image, as contrast will not be washed out, better confirming stenting of the ostium. As the use of this apparatus may be significantly faster (e.g., less than 30 seconds, less than 20 seconds, less than 15 seconds), occluding the ostium in this manner during use is safe and effective.

As mentioned, the annular balloon at the distal end region of the ostial positioning catheter may be formed of a highly compliant and thin biocompatible material. For example, the ballon may be formed of a material having a durometer of between about 5 ShoreA and about 75 ShoreA (e.g., between about 5 ShoreA and about 70 ShoreA, between about 5 ShoreA and 65 ShoreA, between about 5 ShoreA and 60

ShoreA, etc.). Examples of such materials may include, but are not limited to: medical-grade Styrene Ethylene Butylene Styrene (SEBS) thermoplastic elastomers (TPEs) such as SEBS Proflex™, medical-grade thermoplastic polyurethanes (TPUs) such as Chronoprene® and/or Rezalloy™ and/or Pellethane™, medical-grade thermoplastic polyesters such as Neusoft™, a thermoplastic vulcanizate (TPV) such as Santoprene™ or other polypropylene (PP) thermoplastic matrix materials that include dynamically vulcanized EPDM rubber and or a blend including one or more of these such as PolyBlend™.

Figure 3C:
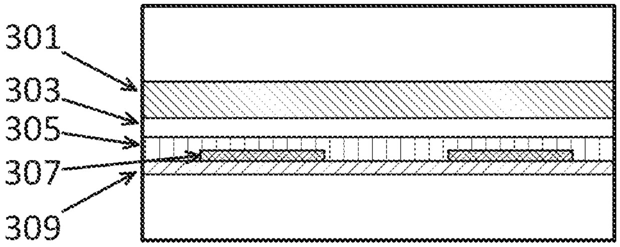
FIG. 3C shows a section through a region of the wall of the apparatus shown in FIG. 1.

In general, once inflated, only the distal end region of the balloon may engage with the ostium (e.g., with the aorta in some examples). FIGS. 3A-3C illustrate details of the distal end region of the ostial positioning catheter, including the annular balloon.

The distal end region of the distal reinforced shaft of the ostial positioning catheter may include a distal, radiopaque tip 306. In FIG. 3A the distal end of an ostial positioning catheter is shown in a first configuration in which the annual (e.g., toroidal) compliant balloon 303 is shown un-inflated/collapsed. The compliant balloon 303 is bonded to the distal end of the reinforced shaft of the catheter, but may be spaced so that when inflated (as shown in FIG. 3B) the compliant balloon 303 extends distally from the distal end (e.g., tip 306) by a predetermined spacing distance 319 that may be, e.g., between about 0.4 and 2 mm (e.g., between about 0.4-1 mm, between about 0.4-0.6 mm, etc.).

The distal tip 306 of the ostial positioning catheter may include a radiopaque, but soft, region, as shown. For example, the radiopaque (RO) region may be formed of a tungsten loaded PEBAX material. The lumen 371 through the ostial positioning catheter may be lined, e.g., with a lubricous liner 209, such as a polytetrafluoroethylene (PTFE) liner.

FIG. 3C shows a portion of a section (3C in FIG. 3A) through the device, forming a wall of the distal reinforced shaft. The wall in this example includes an outer jacket 301 and a coil jacket 305 forming an inflation lumen 303. A reinforcement, such as a reinforcing coil 307 may be embedded within the coil jacket. The reinforcing coil may be a metal (e.g., nickel titanium, stainless steel, etc.), or polymeric material. The inner wall of the distal reinforced shaft may include a lubricous inner liner 309, coating and/or embedded material.

FIGS. 4A-4B illustrate the annular balloon of the ostial positioning catheter in a deployed configuration, in which the annular balloon 103 is fully inflated. In FIG. 4A the balloon proximal face is configured to receive the outer end of the delivery catheter (e.g., guide catheter) and the balloon distal face is configured to seal around/against the ostia. The balloon is sealed proximally and distally, and the inflation lumen is concentrically coupled to the inner lumen of the balloon, as shown in the enlarged view of region 4B (in FIG. 4A) shown in FIG. 4B. FIG. 4B shows the distal balloon seal 478 and the proximal ballon seal 479, as well as the concentric inflation lumen 480. The balloon surrounds the lumen of the ostial positioning catheter 471, though which a stent deployment catheter and/or guidewire may pass.

Figure 5:
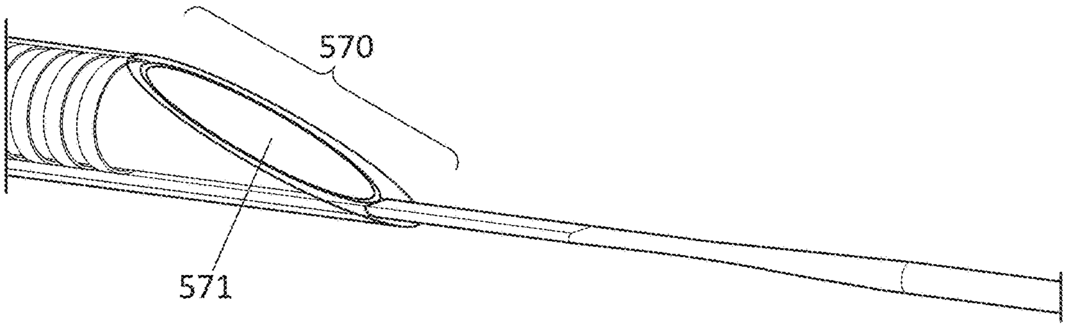
FIG. 5 is a side perspective view of the proximal opening of the distal reinforced shaft of an ostial positioning catheter apparatus, similar to that shown in FIG. 1.

FIG. 5 shows an enlarged view of the proximal end of the distal reinforced region (shaft) of the ostial positioning catheter. In FIG. 5, the proximal end of this reinforced region forms an opening 570 into the lumen of the ostial positioning catheter that is tapered (e.g., with an angle that may be between about 10 degrees and about 60 degrees, e.g., between 15 degrees and 40 degrees, between 20 degrees and 45 degrees, etc.) to enhance ease of inserting materials through it while within the guide catheter or otherwise.

Figure 6:
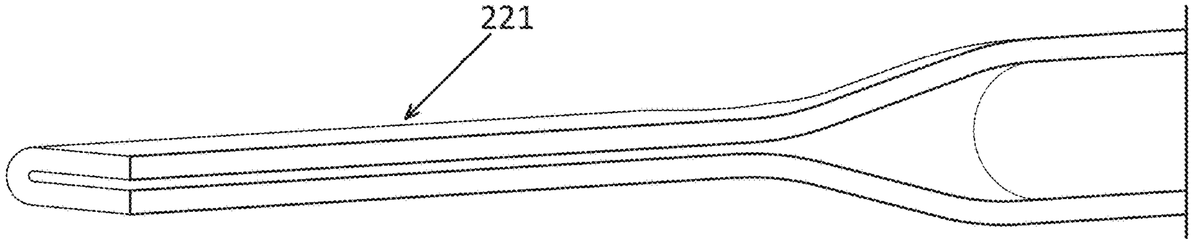
FIG. 6 shows a section through a region of a flattened, rectangular hypotube that is configured to form a proximal portion of an ostial positioning catheter apparatus so that the lumen of the hypotube is in fluid communication with the annular balloon to control inflation.

FIG. 6 shows a section through an example of a flattened region 221 hypotube that may be used to form the proximal hypotube shaft, as described above in reference to FIGS. 2C and 2D.

Figure 7:
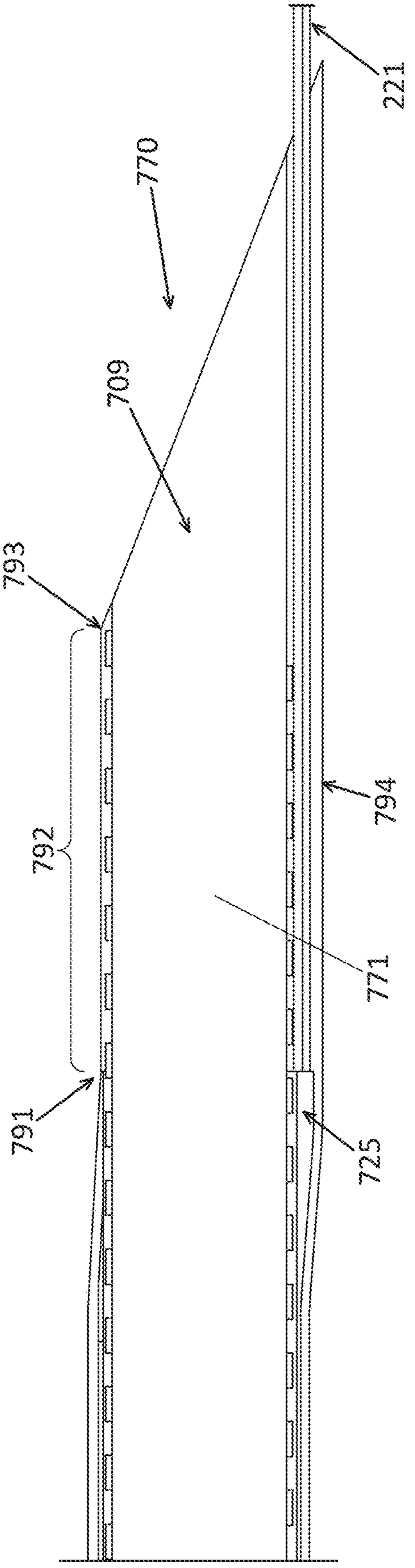
FIG. 7 is a sectional view through the proximal region of the distal reinforced shaft of an ostial positioning catheter apparatus similar to that shown in FIG. 1.

As shown in FIG. 7, the proximal hypotube shaft may be coupled with the distal reinforced shaft to provide a stable coupling transition, while placing the lumen of the hypotube in fluid communication with the inflation lumen for the balloon. FIG. 7 shows details of one example of a section through a wall of the reinforced region. Showing termination of the coil jacket region 791, a proximal fuse region 792 that may seal the inflation lumen to the hypotube, and the coil or braid reinforcement termination 793 before the opening into the lumen. The flattened region of the hypotube 221 is shown sealed within the slot of the reinforced region, and the inflation lumen is in fluid communication with the inflation lumen 725 within the reinforced region. An outer jacket 794 may cover the reinforced region, as shown. The sectional view of FIG. 7 also shows the lumen 771 of the ostial positioning catheter as well as the inner lubricous layer or lining 709 and the tapered opening into the lumen 770 of the ostial positioning catheter.

Figure 8:
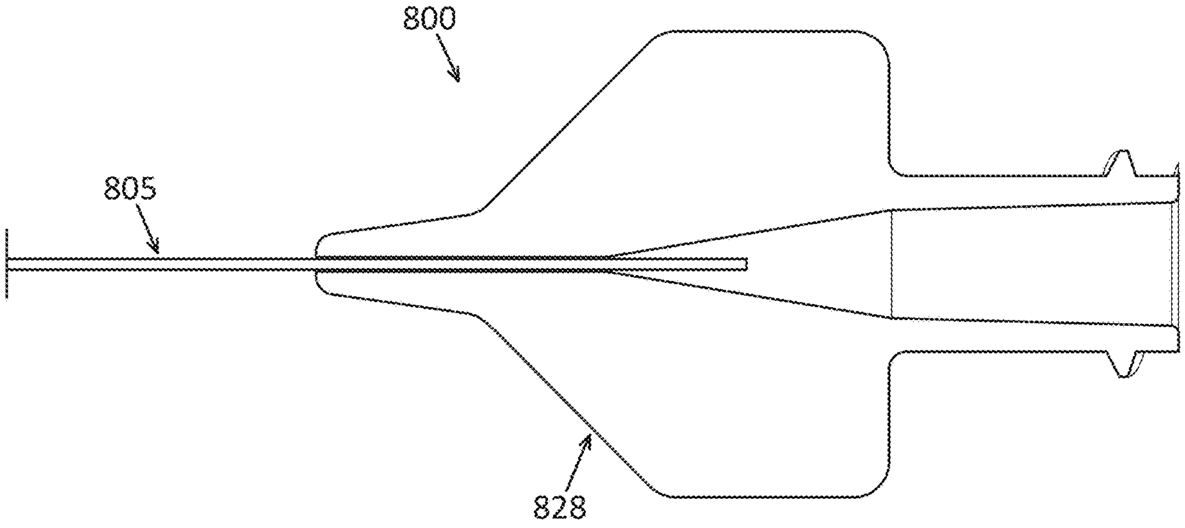
FIG. 8 is a side view of the proximal engagement region (showing the proximal end region, e.g., handle, of an ostial positioning catheter) that is configured to interface and/or be integral with an integrated stopcock.
Figure 9:
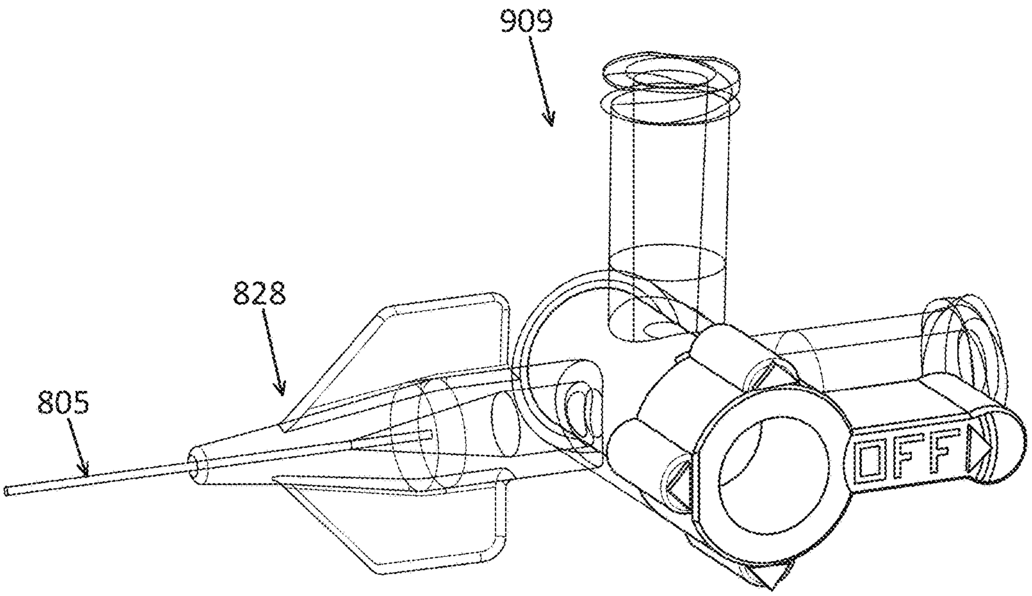
FIG. 9 is a perspective view of the proximal integrated stopcock, forming a proximal end region (e.g., proximal handle), of an ostial positioning catheter simar to that shown in FIG. 1.
Figure 10:
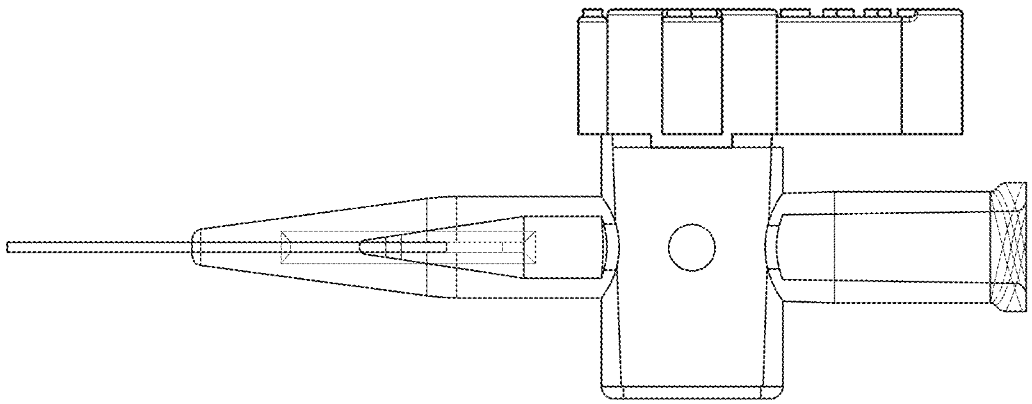
FIGS. 10 and 11 show side and top views, respectively of the proximal end, including the integrated stopcock, of the apparatus shown in FIG. 1.
Figure 11:
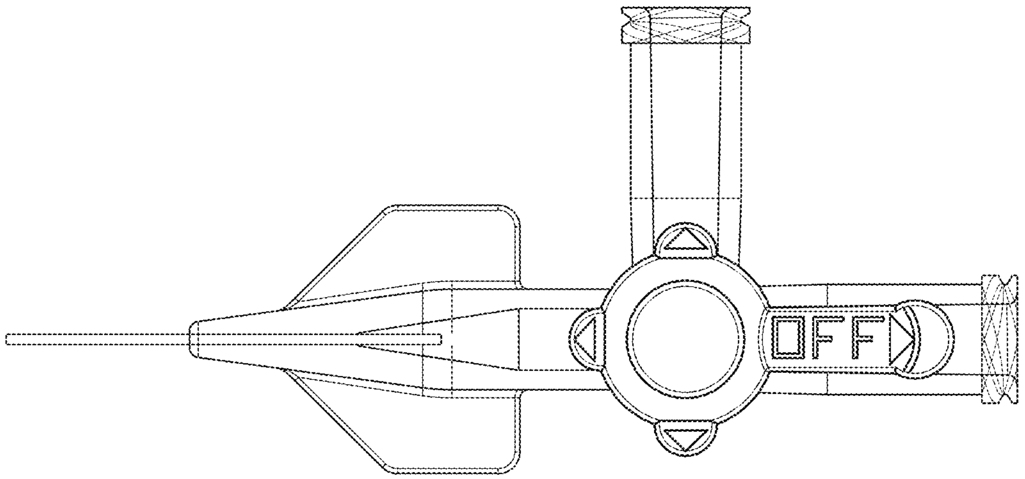

FIG. 8 shows an example of a proximal connector 800 comprising an inflation hub 828 coupled to the proximal end of the hypotube 808. In some examples, shown in FIG. 9, the proximal connector 800 may also include (or may be coupled with) a stopcock 909. In some case the stopcock may be integrally connected to the inflation hub. FIGS. 10 and 11 illustrate views of a stopcock that is integrally formed with the inflation hub.

Stent Positioning at the Ostium of a Blood Vessel

Figure 12A:
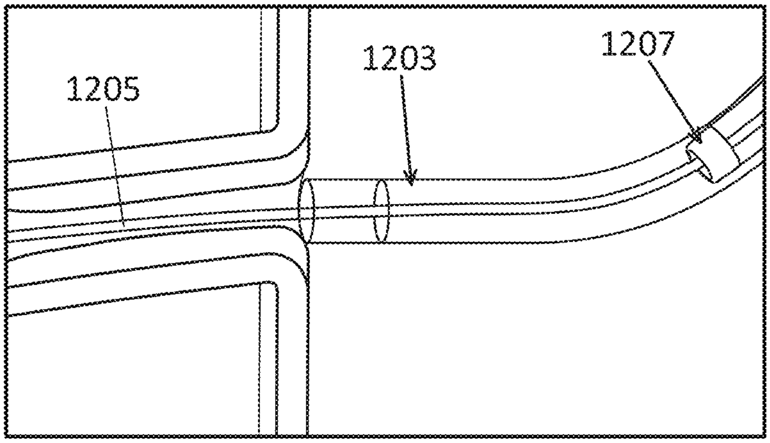
FIGS. 12A-12E illustrate one method of using an ostial positioning catheter as described herein relative to an ostium.
Figure 12B:
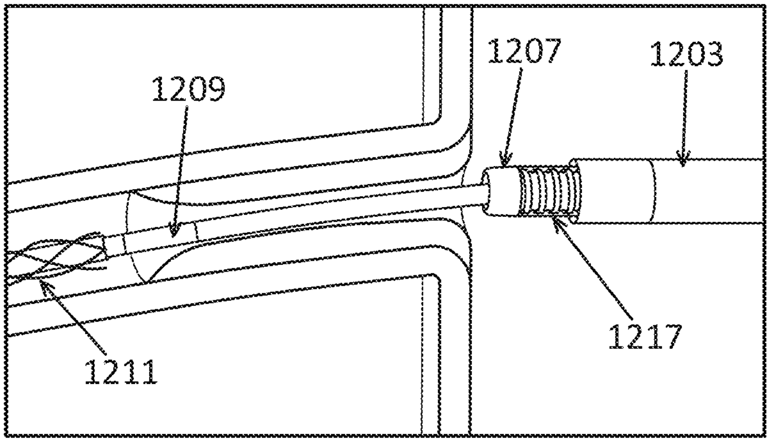
Figure 12C:
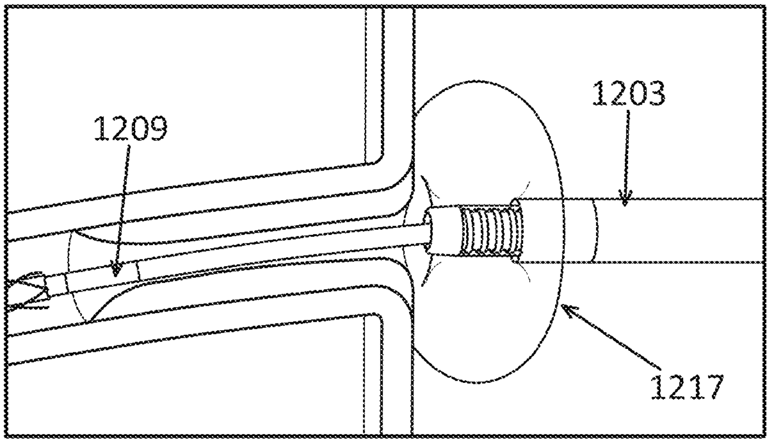
Figure 12D:
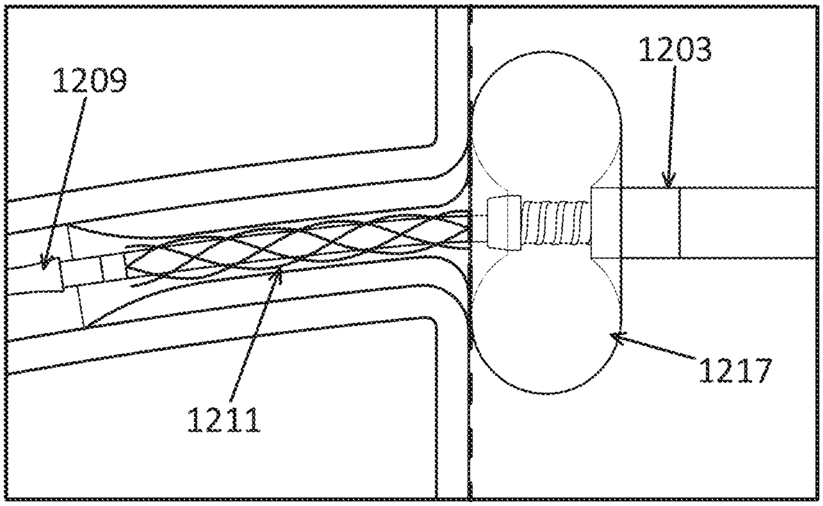
Figure 12E:
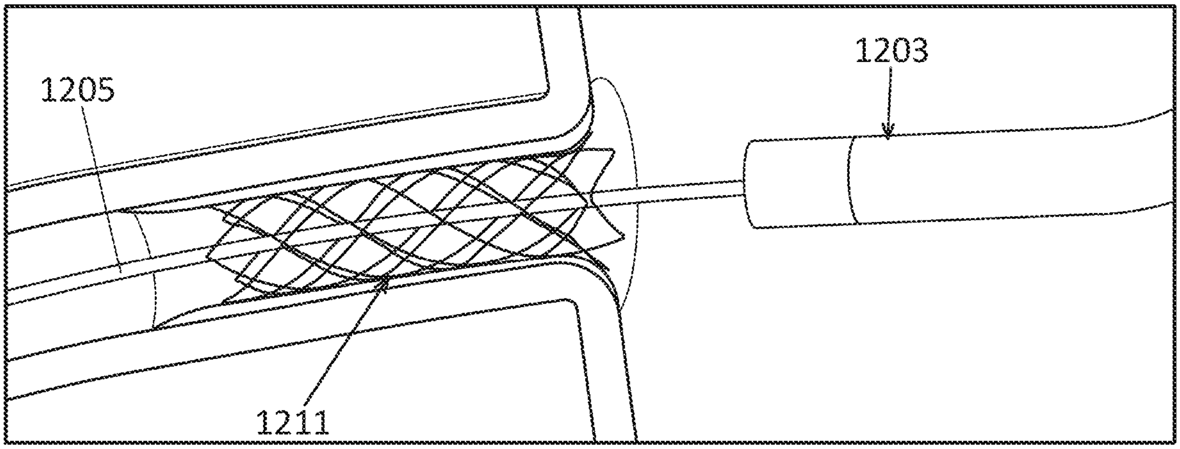

FIGS. 12A-12E illustrate one example of a method of using an apparatus as described herein to position and deploy a stent within an ostium. In FIG. 12A, a guide catheter 1203 is engaged with the coronary ostia and a guidewire 1205 is inserted into coronary artery. The ostial positioning catheter 1207 is shown inserted into guide catheter and positioned just proximally to distal tip. In FIG. 12B, a stent delivery catheter 1209 (loaded with a stent 1211 on a deployment balloon) is introduced into patient thorough the guide catheter 1203 and through the ostial positioning catheter 1207 and delivered to coronary artery. Once positioned, the ostial positioning catheter 1207 is advanced distally until the balloon region 1217 is outside distal tip of guide catheter. In FIG. 12C the balloon 1217 of the ostial positioning catheter 1207 is inflated and pressed against coronary ostia using fluoroscopic guidance. The guide catheter distal tip may be held (or pressed) against proximal edge of ostial positioning balloon 1217. In FIG. 12D, the stent delivery catheter 1209 is withdrawn proximally until a proximal marker on the stent delivery catheter is aligned with edge of the ostial positioning balloon 1217. The stent balloon on the stent delivery catheter 1209 under the stent 1211 is then ready to be inflated to deploy the stent. In FIG. 12E, the stent 1211 has been deployed, and the stent balloon catheter has been removed, as has the ostial positioning catheter.

In general, a method of positioning an ostial stent using the apparatuses described herein may generally include positioning a guide catheter at an ostia of a blood vessel (e.g., into a coronary artery). The method may then include advancing a guidewire through the ostial lesion into the more distal portion of the targeted coronary artery. An ostial positioning catheter may then be advanced through the guide catheter and over the guidewire, but may remain (e.g., in a distal end region) in the guide catheter. A stent delivery catheter may then be advanced through the guide catheter, over the guidewire, and through the tubular portion (e.g., the distal reinforced shaft) of the ostial positioning catheter, past the ostia into the coronary artery. The guide catheter may then be slightly withdrawn from ostial engagement, and the ostial positioning catheter may be advanced out of the guide catheter so that a distal end of the ostial positioning catheter is proximal to the ostia and outside of the guide catheter. This distal end region includes the annular, toroidal ballon. The method may then include inflating the annular, toroidal balloon of the ostial positioning catheter, and advancing the distal side of the annular, toroidal balloon against a tissue around the ostia, and pushing on the proximal plane of the inflated balloon so as to "sandwich" the balloon between the aortic wall and the tip of the guide catheter. With the annular balloon held (e.g., sealed) around the ostia, the stent deployment catheter may be moved (e.g., withdrawn). Withdrawing the stent deployment catheter towards the ostial positioning catheter may be performed to align a proximal end of a stent on the stent deployment catheter with the distal portion of the annular, toroidal balloon, and with the proximal marker of the stent delivery system that is aligned with a radio-opaque tip marker of the ostial positioning catheter. Once positioned, the stent may be deployed from the stent delivery catheter to expand the coronary artery, so that the proximal stent end is aligned with the coronary ostium.

Finally, the annular, toroidal balloon may be deflated, and the ostial positioning catheter may be removed back proximally through the guide catheter.

Figure 13A:
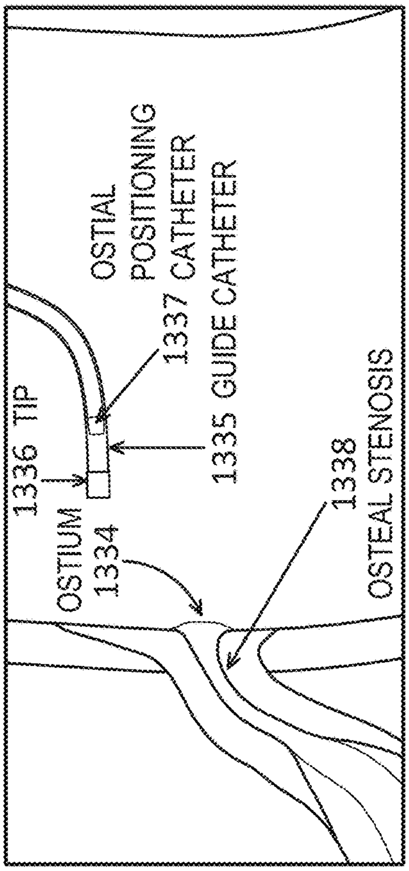
FIGS. 13A-13S illustrate one example of a method of using an ostial positioning apparatus to stent an ostium as described herein.
Figure 13B:
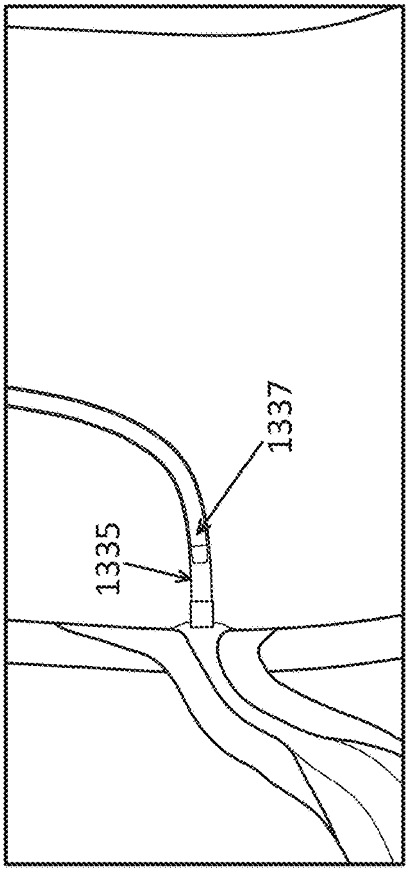
Figure 13C:
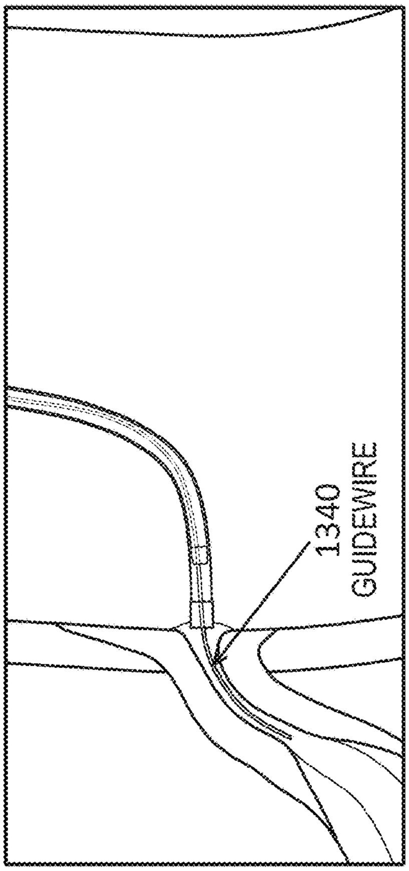
Figure 13D:
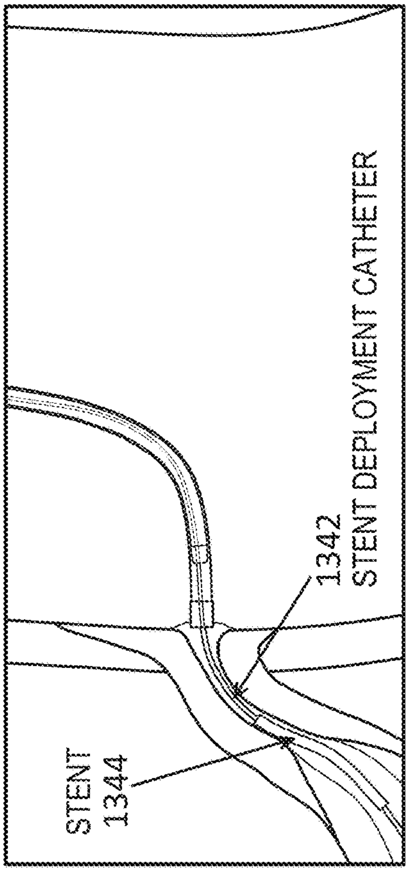
Figure 13E:
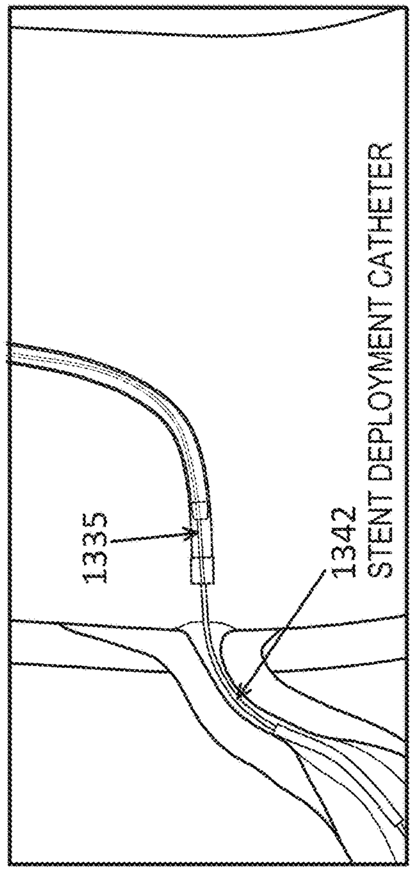
Figure 13F:
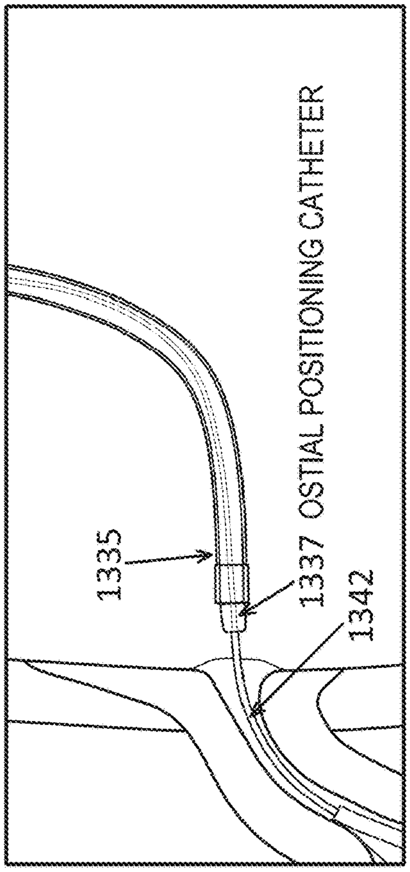
Figure 13G:
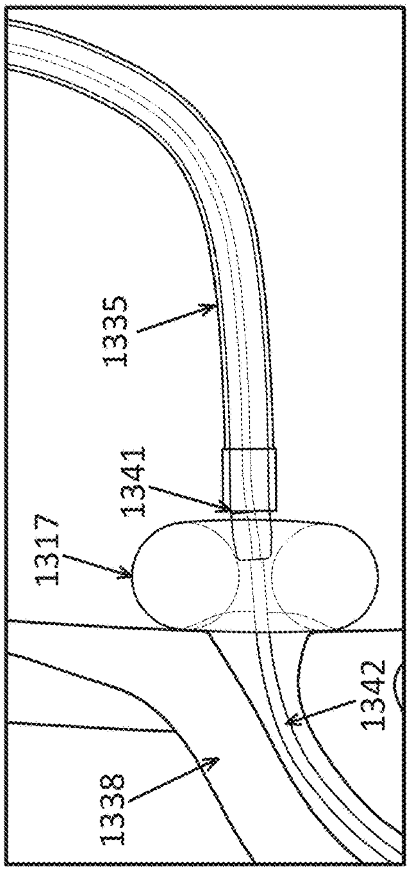
Figure 13H:
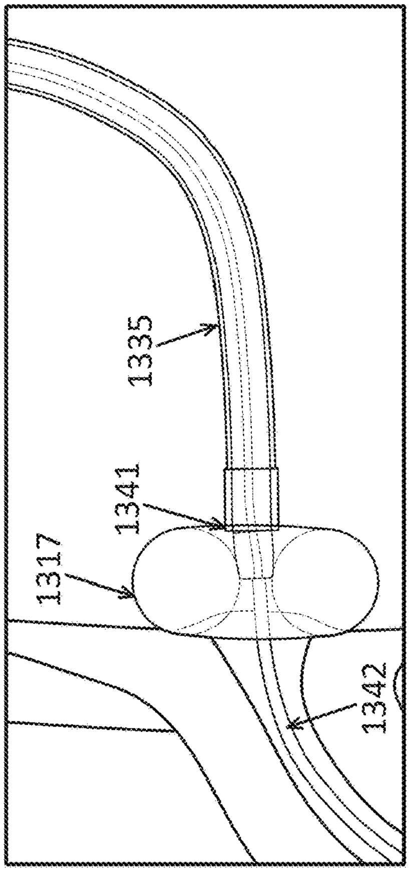
Figure 13I:
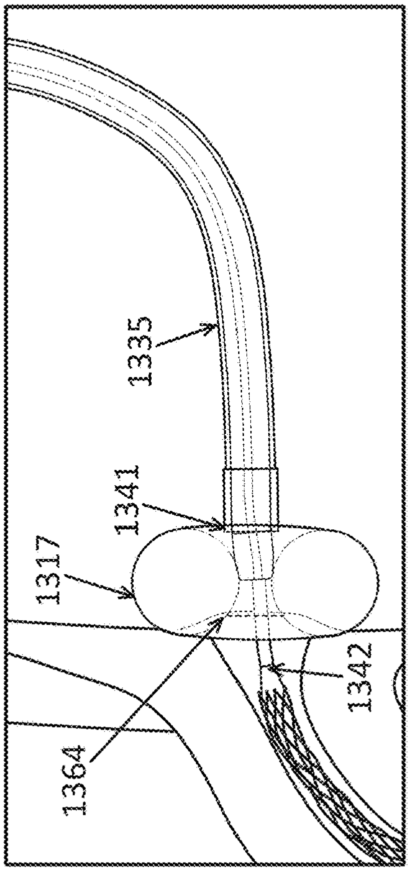
Figure 13J:
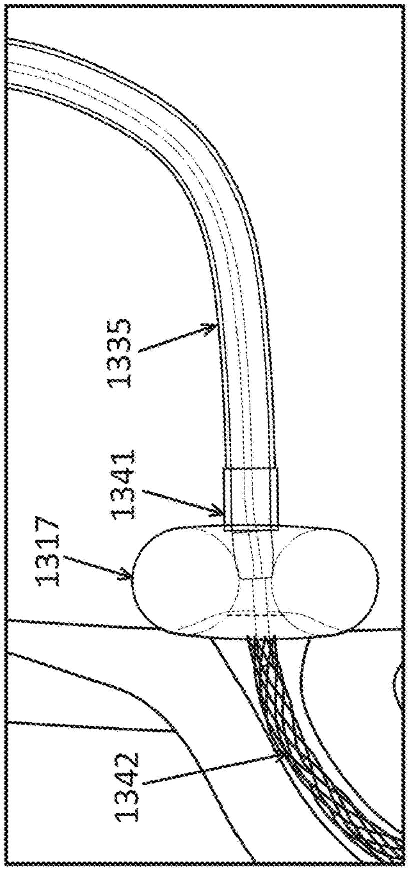
Figure 13K:
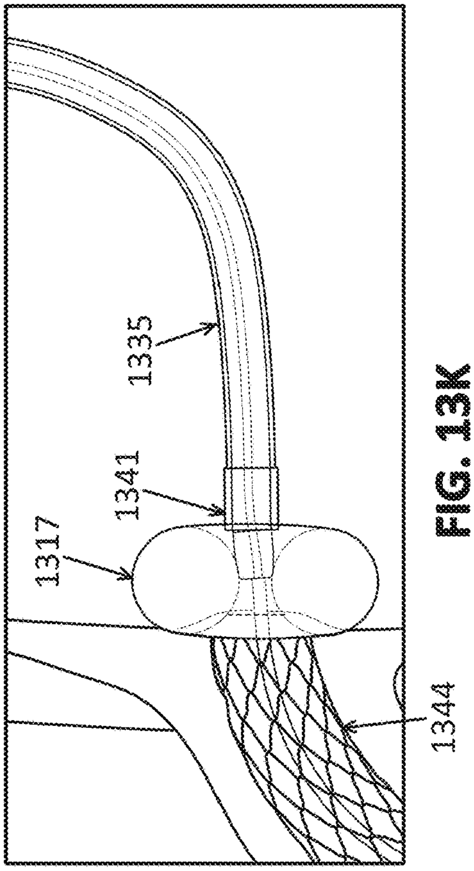
Figure 13L:
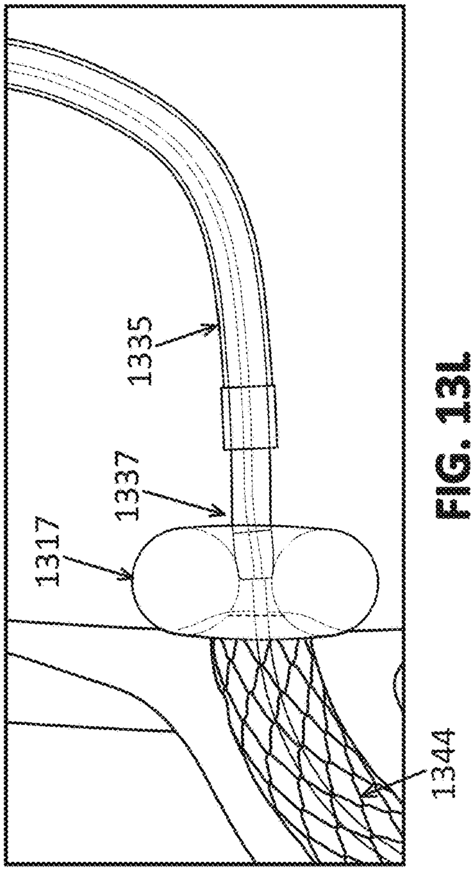
Figure 13M:
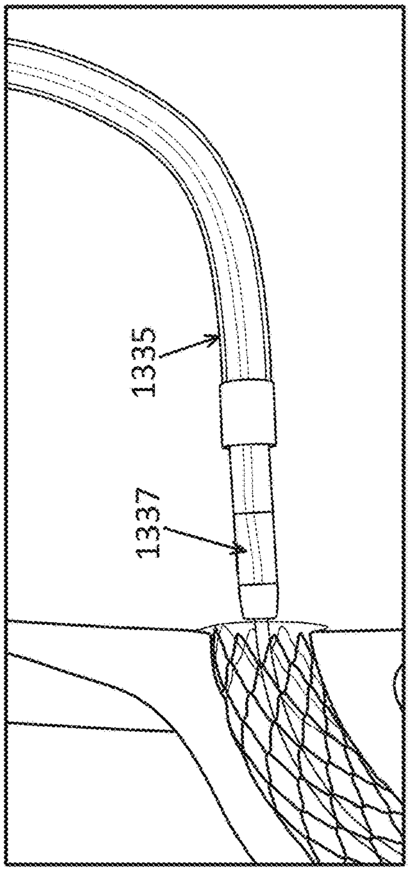
Figure 13N:
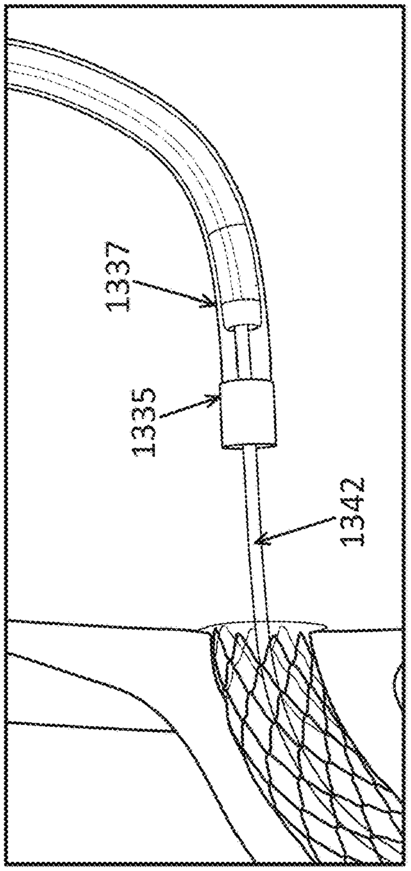
Figure 13O:
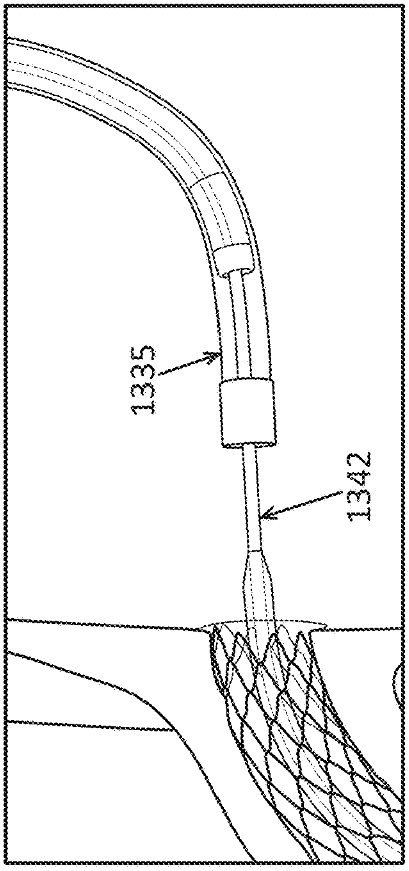
Figure 13P:
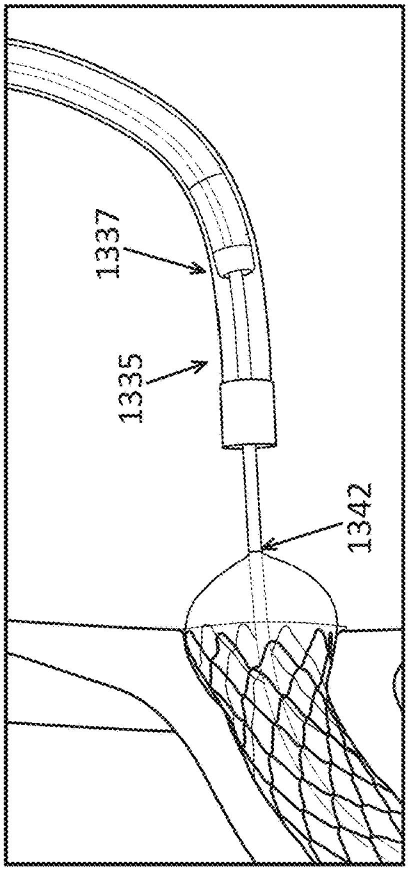
Figure 13Q:
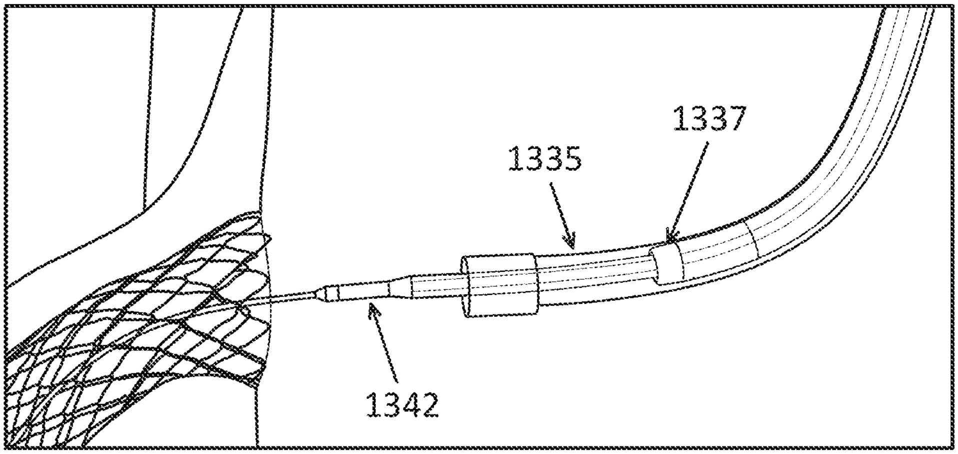
Figure 13R:
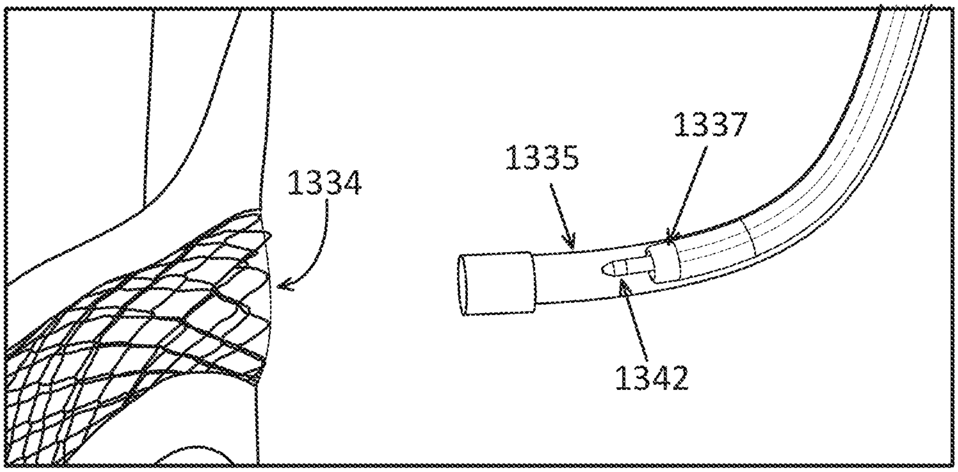
Figure 13S:
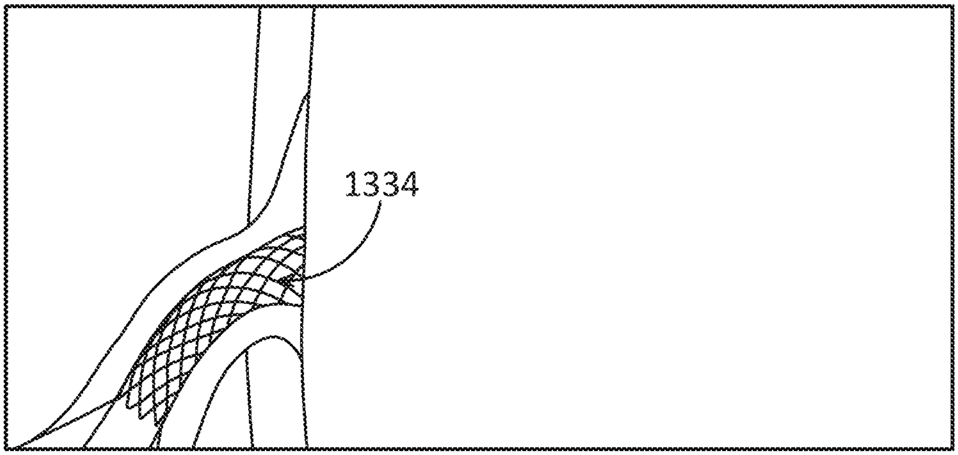

FIGS. 13A-13S illustrate an example of this method of stenting an ostium using the apparatus described herein. In FIG. 13A the ostium 1334 is shown having an osteal stenosis 1338. The guide catheter 1335 including an atraumatic and radiopaque distal tip 1336 is inserted into the vessel coupled to the ostium. In some examples the ostial positioning catheter 1337 may optionally be within the lumen of the guide catheter 1335. Alternatively, the ostial positioning catheter 1337 may be outside of (or more proximally within) the guide catheter and inserted later. As shown in FIGS. 13B and 13C, the tip of the guide catheter 1335 may be directed to the opening of the ostium, e.g., using one or more guidewires passing through the guide catheter. As shown in FIG. 13C a guidewire 1340 may be inserted into the ostium from the guide catheter. Optionally the osteal stenosis 1338 may be broken up (fractured, expanded, etc.) by first using an expansion balloon catheter or other apparatus. For example, an expansion balloon catheter may be delivered over the stent and positioned within the stenosis and the balloon expanded, e.g., to break/crack the stenosis.

As shown in FIG. 13D a stent deployment catheter 1342 may then be deployed through the ostial positioning catheter 1337 and/or through the guide catheter 1335 until it is beyond the ostium, as shown. A stent 1344 is preloaded onto the stent deployment catheter 1342. The ostial positioning catheter 1337 may then be deployed out of the guide catheter, after backing the guide catheter slightly away from the ostium, as shown in FIG. 13E, to make room for the annular balloon of the ostial positioning catheter 1337 to be deployed distally out of the guide catheter. In FIG. 13F, the ostial positioning catheter 1337 is shown being deployed out of the guide catheter just proximal to the ostium (the opening into the ostium). Thereafter, the annular balloon 1317 may be deployed, as shown in FIG. 13G. In this example the balloon expands to a diameter that is greater than the diameter of the ostium, while the stent deployment catheter 1342 is extended distally into the ostium, though the stenotic region 1338 of the ostium. The annular balloon 1317 may then be driven against the face of the ostium to seal the ostium, e.g., by driving the ostial positioning catheter distally and/or by driving the stent catheter 1335 distally against the back side (the distal face) of the balloon 1317 so that the atraumatic tip region 1341 is pushed against the proximal face of the balloon 1317, and the distal face of the balloon is pushed against (and/or seals against) the ostium as shown in FIG. 13H. In FIG. 13I the stent delivery catheter 1342 is pulled proximally backwards until a proximal end/edge of the stent 1344 is aligned with the ostial face, as determined by the distal end face 1364 of the ostial positioning catheter which is maintained sealed against the wall of the blood vessel, e.g., by pushing either or both the ostial positioning catheter and/or the guide catheter 1335 distally to drive the deployed annular balloon against the ostium, as shown in FIGS. 13I-13J. Once the stent deployment catheter 1342 (and the stent 1344 loaded thereon) is aligned with the balloon (e.g., with the plane of the ostial opening), the user, e.g., a doctor, nurse, technician, clinician, etc., can deploy the stent by inflating the stent deployment balloon on the stent deployment catheter 1342, as shown in FIGS. 13K-13L. The proximal end of the stent 1344 is limited by the annulus balloon, which may be stably held against the annulus, as described above, e.g., by pushing the ostial positioning catheter 1337 distally. Once the stent is initially deployed, as shown in FIG. 13L-13M. the balloon 1317 of the ostial positioning catheter 1337 may be deflated and the ostial positioning catheter 1337 withdrawn back into the guide catheter 1335, as shown in FIGS. 13M and 13N. The deployment balloon of the stent deployment catheter 1342 may the been deflated, either passively or manually, leaving the stent in position, as shown in FIGS. 13K-130. The proximal end of the stent may optionally be expanded to form a trumpet shape (shown in FIG. 13P) by withdrawing a portion of the stent deployment catheter 1342 proximally so that the balloon of the stent deployment catheter 1342 may again be expanded. Finally, as shown in FIGS. 13Q-13R, the stent deployment catheter 1342 may be withdrawn proximally into the guide catheter 1335 and/or the ostial positioning catheter 1337. Finally, as shown in FIG. 13S, the guide catheter may be fully withdrawn, leaving the stented ostium.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element, or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for applying a stent to an ostium of a blood vessel, the system comprising:

a guide catheter having a guide catheter lumen;

an ostial positioning catheter configured to slideably fit within the guide catheter lumen, the ostial positioning catheter comprising a distal reinforced shaft having a length of less than 20 cm and a lumen extending therethrough, an annular sealing balloon at a distal end region of the distal reinforced shaft, and a hypotube extending proximally from a longitudinal side of the distal reinforced shaft, wherein the hypotube comprises an inflation lumen in fluid communication with the annular sealing balloon through the distal reinforced shaft; and a stent deployment catheter configured to slideably fit within the ostial positioning catheter, the stent deployment catheter comprising the stent over a deployment balloon, wherein, when the annular sealing balloon is extended distal of a distal tip of the guide catheter and the annular sealing balloon is inflated, the distal tip of the guide catheter is configured to press against a proximal side of the annular sealing balloon.

2. The system of claim 1, further comprising a guidewire configured to fit through a lumen of the stent deployment catheter.

3. The system of claim 1, wherein the stent deployment catheter extends through the lumen of the ostial positioning catheter and further wherein the ostial positioning catheter extend through the guide catheter lumen.

4. The system of claim 1, wherein a distal region of the hypotube is flattened.

5. The system of claim 4, wherein a flattened distal region of the hypotube engages with a longitudinal slot through a wall of the distal reinforced shaft so that the inflation lumen of the hypotube is in fluid communication with an inflation path through a wall of the distal reinforced shaft that is in fluid communication with the annular sealing balloon.

6. The system of claim 4, wherein the flattened distal region of the hypotube has a rectangular or elliptical transverse cross-section.

7. The system of claim 1, wherein the length of the distal reinforced shaft is 2 cm or less.

8. The system of claim 1, wherein the distal reinforced shaft comprises a helically wound metal reinforcement.

9. The system of claim 1, wherein the lumen of the distal reinforced shaft comprises a lubricious hydrophilic outer surface.

10. The system of claim 1, wherein the distal reinforced shaft has a greater flexibility than the hypotube.

11. The system of claim 1, further comprising an inflation hub that is integrally coupled with a stopcock.

12. The system of claim 1, wherein the hypotube extends proximally from the longitudinal side of the distal reinforced shaft by greater than 10 cm.

13. The system of claim 1, further comprising a proximal connector, the proximal connector comprising a stopcock configured to control flow into/out of an inner lumen of the hypotube.

14. The system of claim 1, wherein a maximum outer diameter of the ostial positioning catheter with the annular sealing balloon uninflated is 8 F or smaller.

15. The system of claim 1, wherein the hypotube is mounted off-axis with the distal reinforced shaft.

16. The system of claim 1, wherein the hypotube has an outer diameter than is less than half of the outer diameter of the distal reinforced shaft.

17. A method of positioning a stent, the method comprising:

positioning a guide catheter at an ostium of a blood vessel;

extending an expansion ballon catheter from the guide catheter and into the ostium, and expanding the expansion ballon catheter to break a stenosis within the ostium, then withdrawing the expansion ballon catheter out of the guide catheter;

advancing a stent delivery catheter through the guide catheter and into the ostium;

positioning an ostial positioning catheter through the guide catheter and over the stent delivery catheter so that a distal end of the ostial positioning catheter is proximal to the ostia and outside of the guide catheter;

inflating an annular, toroidal balloon at a distal end region of the ostial positioning catheter;

holding a distal side of the annular, toroidal balloon against a tissue around the ostium to occlude blood flow through the ostium;

moving the stent delivery catheter through the ostial positioning catheter to align a proximal end of the stent on the stent delivery catheter with the annular, toroidal balloon;

deploying the stent from the stent delivery catheter to expand a coronary artery; and deflating the annular, toroidal balloon and withdrawing the ostial positioning catheter through the guide catheter.

18. The method of claim 17, further comprising flaring the proximal end of the stent by withdrawing the stent delivery catheter proximally and expanding the stent delivery catheter to further expand the proximal end of the stent.

19. The method of claim 17, wherein holding the distal side of the annular, toroidal balloon against the tissue around the ostium comprises pushing the guide catheter distally against a proximal face of the annular, toroidal balloon.

20. A system for applying a stent to an ostium of a blood vessel, the system comprising:

a guide catheter having a guide catheter lumen and a distal tip;

an ostial positioning catheter configured to slide within the guide catheter lumen, the ostial positioning catheter comprising:

a distal reinforced shaft having a lumen extending therethrough;

an annular sealing balloon at a distal end region of the distal reinforced shaft, wherein, when the annular sealing balloon is extended distal of the distal tip of the guide catheter and the annular sealing balloon is inflated, a proximal side of the annular sealing balloon is configured to press against the distal tip of the guide catheter; and a hypotube extending proximally from a longitudinal side of the distal reinforced shaft, wherein the hypotube comprises an inflation lumen in fluid communication with the annular sealing balloon; and a stent deployment catheter configured to slide within the lumen of the distal reinforced shaft.

* * * * *